(12) United States Patent
Hirohara et al.

(10) Patent No.: US 7,222,962 B2
(45) Date of Patent: May 29, 2007

(54) OPTHALMIC MEASURING APPARATUS

(75) Inventors: Yoko Hirohara, Tokyo (JP); Hiroaki Hashimoto, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 491 days.

(21) Appl. No.: 10/683,126

(22) Filed: Oct. 14, 2003

(65) Prior Publication Data
US 2004/0130678 A1    Jul. 8, 2004

(30) Foreign Application Priority Data
Oct. 17, 2002    (JP) ............................... 2002-302435

(51) Int. Cl.
*A61B 3/10* (2006.01)

(52) U.S. Cl. .................................... 351/205

(58) Field of Classification Search ......... 351/200–205
See application file for complete search history.

(56) References Cited

U.S. PATENT DOCUMENTS 5,929,970 A * 7/1999 Mihashi ...................... 351/205

FOREIGN PATENT DOCUMENTS

| JP | 2580215 B2 | 11/1996 |
|---|---|---|
| JP | 2001-204690 | 10/2000 |
| JP | 2002-204784 A | 7/2002 |
| WO | WO 01/47407 | 12/2000 |

* cited by examiner

*Primary Examiner*—Huy Mai
*Assistant Examiner*—M. Hasan
(74) *Attorney, Agent, or Firm*—Foley & Lardner LLP

(57) ABSTRACT

An optical characteristic of an eye is obtained which can not be measured through a uniform adjustment because of a large difference in the distribution of a refractive index, or the like. An arithmetic part first selects an interlock mode, and performs an alignment adjustment. Next, the arithmetic part measures refraction, and interlocks and moves a first illumination optical system and a first light receiving optical system on the basis of the refraction. The arithmetic part obtains a density distribution of point images obtained from a first light receiving part, and judges whether a measurement can be made for each area on the basis of the density. The arithmetic part makes an adjustment so that an unmeasurable area becomes measurable, and creates a composite point image from plural signals obtained in a process of the adjustment. Further, the arithmetic part uses the composite point image to perform a Zernike analysis, obtains the optical characteristic and outputs it on a display part or the like.

9 Claims, 18 Drawing Sheets

FIG.1

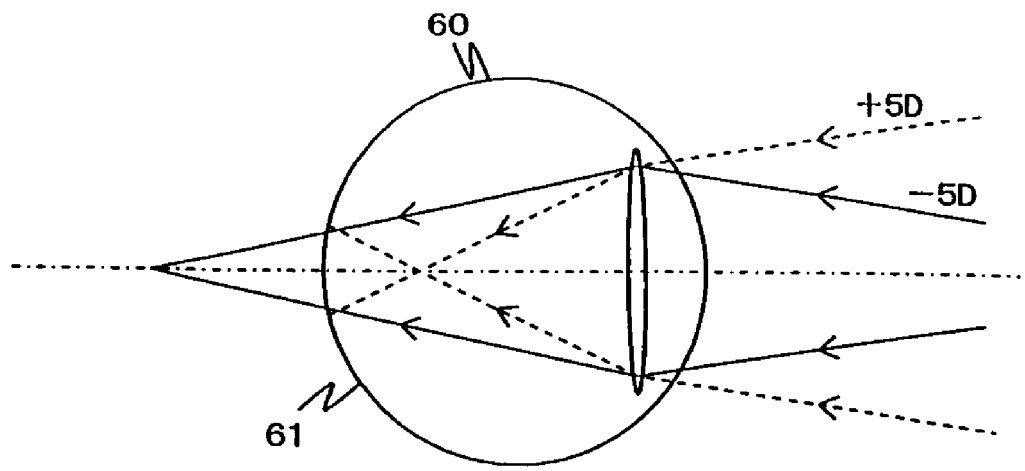
AT TIME OF POSITIONAL SHIFT OF PROJECTION SIDE
(A)
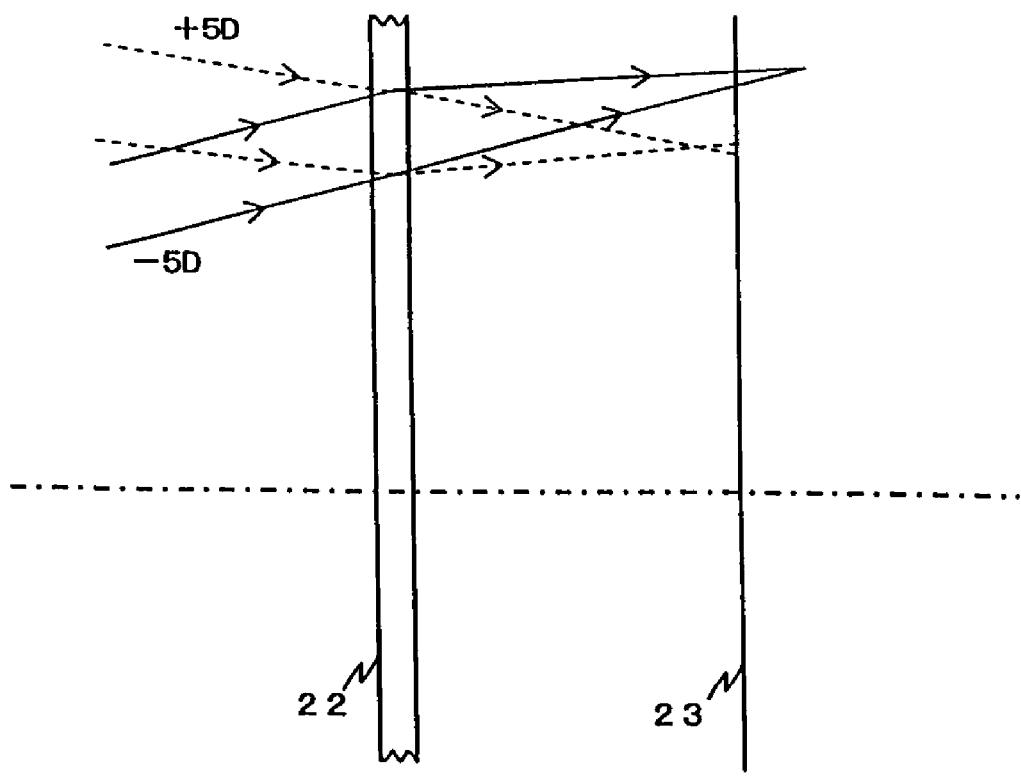
AT TIME OF POSITIONAL SHIFT OF LIGHT RECEIVING SIDE
(B)
FIG.5

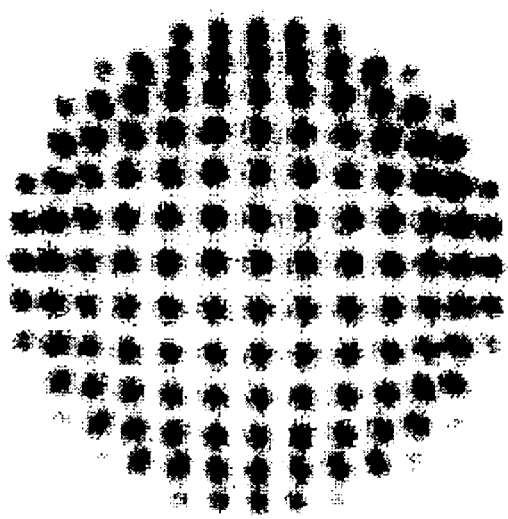
PROJECTION SIDE +5 D
(A)
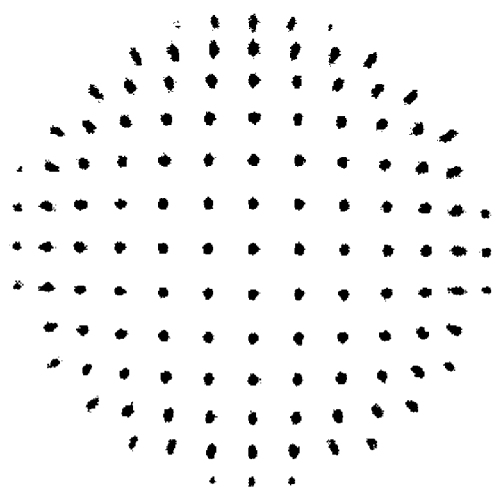
PROJECTION SIDE −5 D
(B)
FIG.6

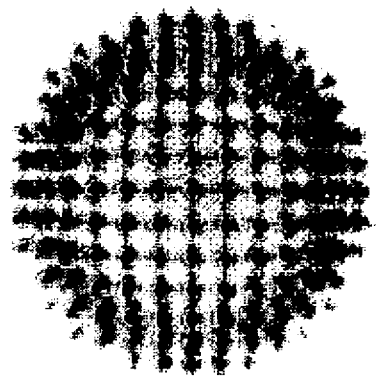
LIGHT RECEIVING SIDE +5 D
(A)
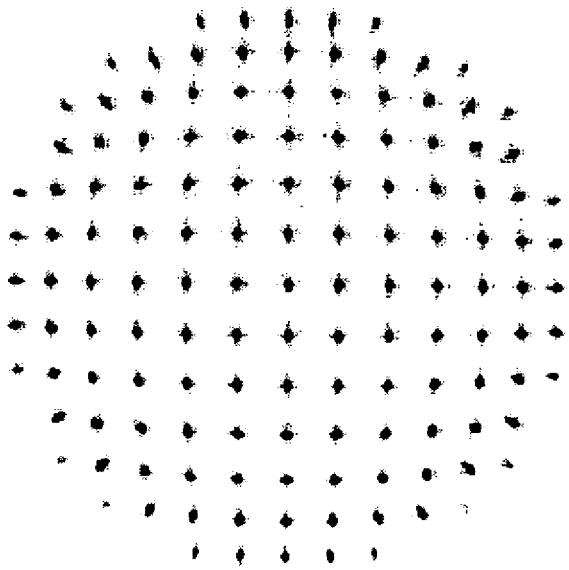
LIGHT RECEIVING SIDE −5 D
(B)
FIG.7

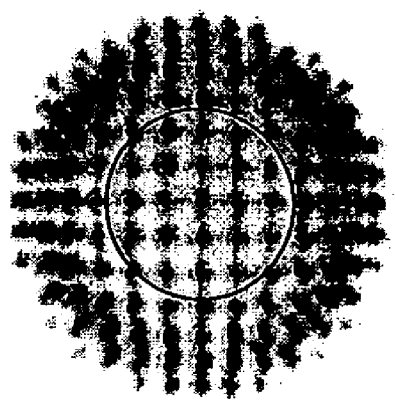
LIGHT RECEIVING SIDE  0D
(A)
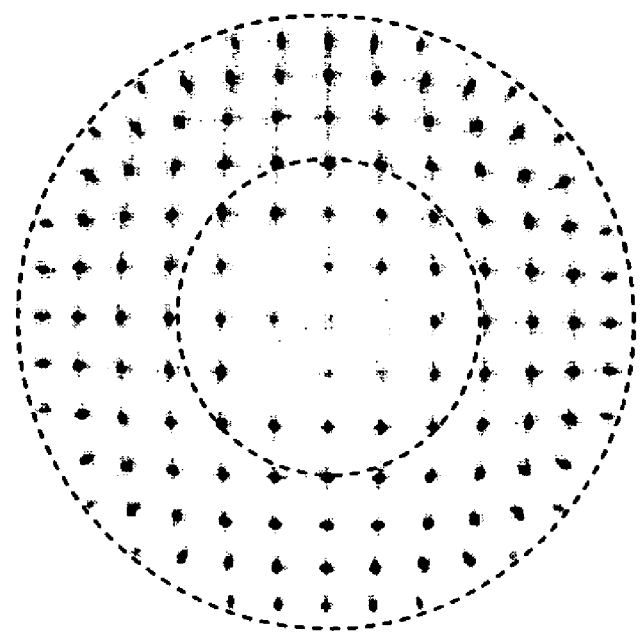
LIGHT RECEIVING SIDE  −5D
(B)
FIG.8

| DATA IDENTIFIER | MEASUREMENT CONDITION | | MEASUREMENT RESULT | | |
|---|---|---|---|---|---|
| | PROJECTION SIDE D VALUE | LIGHT RECEIVING SIDE D VALUE | AREA IDENTIFIER | MEASURABLE IDENTIFICATION INFORMATION | MEASUREMENT VALUE (POINT IMAGE COORDINATES) |
| | | | 1 | ○ | $(X_1, Y_1) \cdots$ |
| | | | 2 | ○ | $(X_8, Y_8) \cdots$ |
| | | | 3 | × | $(X_{20}, Y_{20}) \cdots$ |
| | | | ⋮ | ⋮ | ⋮ |
| | | | ⋮ | ⋮ | ⋮ |

(A) MEASUREMENT DATA

| DATA IDENTIFIER | INFERENCE RESULT | | |
|---|---|---|---|
| | AREA IDENTIFIER | MEASURABLE IDENTIFICATION INFORMATION | INFERENCE VALUE (POINT IMAGE COORDINATES) |
| | 1 | ○ | $(X_{1a}, Y_{1a}) \cdots$ |
| | 2 | ○ | $(X_{8a}, Y_{8a}) \cdots$ |
| | 3 | × | $(X_{20a}, Y_{20a}) \cdots$ |
| | ⋮ | ⋮ | ⋮ |
| | ⋮ | ⋮ | ⋮ |

(B) INFERENCE DATA

FIG.9

$$\begin{bmatrix}
i & 2j-i & \\
0 & 0 & 1 \\
1 & -1 & r\sin(t) \\
1 & 1 & \cos(t)\,r \\
2 & -2 & r^2\sin(2t) \\
2 & 0 & 2r^2-1 \\
2 & 2 & r^2\cos(2t) \\
3 & -3 & r^3\sin(3t) \\
3 & -1 & (3r^3-2r)\sin(t) \\
3 & 1 & (3r^3-2r)\cos(t) \\
3 & 3 & r^3\cos(3t) \\
4 & -4 & r^4\sin(4t) \\
4 & -2 & (4r^4-3r^2)\sin(2t) \\
4 & 0 & 6r^4-6r^2+1 \\
4 & 2 & (4r^4-3r^2)\cos(2t) \\
4 & 4 & r^4\cos(4t) \\
5 & -5 & r^5\sin(5t) \\
5 & -3 & (5r^5-4r^3)\sin(3t) \\
5 & -1 & (10r^5-12r^3+3r)\sin(t) \\
5 & 1 & (10r^5-12r^3+3r)\cos(t) \\
5 & 3 & (5r^5-4r^3)\cos(3t) \\
5 & 5 & r^5\cos(5t) \\
6 & -6 & r^6\sin(6t) \\
6 & -4 & (6r^6-5r^4)\sin(4t) \\
6 & -2 & (15r^6-20r^4+6r^2)\sin(2t) \\
6 & 0 & 20r^6-30r^4+12r^2-1 \\
6 & 2 & (15r^6-20r^4+6r^2)\cos(2t) \\
6 & 4 & (6r^6-5r^4)\cos(4t) \\
6 & 6 & r^6\cos(6t)
\end{bmatrix}$$

FIG.17

$$\begin{array}{cc}
i & 2j-i \\
\begin{bmatrix}
0 & 0 \\
1 & -1 \\
1 & 1 \\
2 & -2 \\
2 & 0 \\
2 & 2 \\
3 & -3 \\
3 & -1 \\
3 & 1 \\
3 & 3 \\
4 & -4 \\
4 & -2 \\
4 & 0 \\
4 & 2 \\
4 & 4 \\
5 & -5 \\
5 & -3 \\
5 & -1 \\
5 & 1 \\
5 & 3 \\
5 & 5 \\
6 & -6 \\
6 & -4 \\
6 & -2 \\
6 & 0 \\
6 & 2 \\
6 & 4 \\
6 & 6
\end{bmatrix} &
\begin{matrix}
1 \\
y \\
x \\
2yx \\
2x^2 + 2y^2 - 1 \\
x^2 - y^2 \\
3yx^2 - y^3 \\
3yx^2 + 3y^3 - 2y \\
3x^3 + 3xy^2 - 2x \\
x^3 - 3xy^2 \\
4yx^3 - 4y^3 x \\
8yx^3 + 8y^3 x - 6yx \\
6x^4 + 12x^2 y^2 + 6y^4 - 6x^2 - 6y^2 + 1 \\
4x^4 - 4y^4 - 3x^2 + 3y^2 \\
x^4 - 6x^2 y^2 + y^4 \\
5yx^4 - 10y^3 x^2 + y^5 \\
15yx^4 + 10y^3 x^2 - 5y^5 - 12yx^2 + 4y^3 \\
10yx^4 + 20y^3 x^2 + 10y^5 - 12yx^2 - 12y^3 + 3y \\
10x^5 + 20x^3 y^2 + 10xy^4 - 12x^3 - 12xy^2 + 3x \\
5x^5 - 10x^3 y^2 - 15xy^4 - 4x^3 + 12xy^2 \\
x^5 - 10x^3 y^2 + 5xy^4 \\
6yx^5 - 20y^3 x^3 + 6y^5 x \\
24yx^5 - 24y^5 x - 20yx^3 + 20y^3 x \\
30yx^5 + 60y^3 x^3 + 30y^5 x - 40yx^3 - 40y^3 x + 12yx \\
20x^6 + 60x^4 y^2 + 60x^2 y^4 + 20y^6 - 30x^4 - 60x^2 y^2 - 30y^4 + 12x^2 + 12y^2 - 1 \\
15x^6 + 15x^4 y^2 - 15x^2 y^4 - 15y^6 - 20x^4 + 20y^4 + 6x^2 - 6y^2 \\
6x^6 - 30x^4 y^2 - 30x^2 y^4 + 6y^6 - 5x^4 + 30x^2 y^2 - 5y^4 \\
x^6 - 15x^4 y^2 + 15x^2 y^4 - y^6
\end{matrix}
\end{array}$$

FIG.18

OPTHALMIC MEASURING APPARATUS

BACKGROUND OF THE INVENTION

1. Field of the Invention

The present invention relates to an ophthalmic measuring apparatus, and particularly to an ophthalmic measuring apparatus for obtaining an optical characteristic of a subject eye by processing plural Hartmann images.

2. Description of the Related Art

In recent years, an optical equipment used for medicine becomes popular, especially in ophthalmology, as an optical characteristic measuring apparatus for examining eye functions, such as eye refraction and adjustment, and the inside of the eye. For example, there exists an apparatus called a photo-refractometer for obtaining the refraction of the subject eye and the retina shape (for example, see patent document 1: Japanese Patent Application No. 2000-351796). The patent document 1 discloses an optical characteristic measuring apparatus which acquires a Hartmann image from a light receiving part, calculates Zernike coefficients on the basis of a distance between a Hartmann plate and the light receiving part, coordinates and the like, calculates the wavefront of the subject eye on the basis of the Zernike coefficients, and displays measurement data, image data corresponding to measurement results, and numerical data. Besides, there is disclosed an apparatus for measuring spherical refractivity, a degree of astigmatism, an astigmatic axial angle and the like from image data of a target image projected on the retina of the subject eye (for example, see patent document 2: Japanese Patent No. 2580215). Incidentally, in the measurement results of these various tests, for example, it becomes important that the subject eye of a patient as a test object is placed under what measurement conditions.

However, in the conventional measuring apparatus for measuring aberrations of the subject eye, in the case where there is a large difference in the distribution of an eye characteristic, such as an eye refractive index, refraction or aberration, there is a case where the measurement can not be made. The large difference like this can occur by, for example, a disease, an injury, a surgical operation or the like.

SUMMARY OF THE INVENTION

In view of the above, an object of the present invention is to provide an ophthalmic measuring apparatus capable of measuring even an eye which can not be measured through a uniform adjustment since a large difference exists in the distribution of an eye characteristic such as a refractive index, refraction or aberration. Besides, an object of the invention is to provide an apparatus in which an automatic adjustment is made so as to obtain point image data necessary for analysis, Hartmann images are acquired, and an optical characteristic is obtained by combining the acquired Hartmann images.

According to first solving means of the invention, an ophthalmic measuring apparatus comprises:

a first illumination optical system including a first light source to emit a light flux of a first wavelength, and for illuminating to be condensed on a vicinity of a retina of a subject eye with a first illumination light flux from the first light source;

a first light receiving optical system including a first conversion member to convert a reflected light flux reflected from the retina of the subject eye into at least 17 beams and a first light receiving part to receive the plural light fluxes converted by the first conversion member as first signals, and for guiding the reflected light flux to the first light receiving part;

first movement means for moving a light condensing position of the first illumination optical system;

second movement means for optically moving the first light receiving part and the first conversion member;

an adjustment part for adjusting positions of the first illumination optical system and the first light receiving optical system by the first and the second movement means to measure the first signals under plural measurement conditions until a measurement of an optical characteristic of the subject eye is enabled by combining the first signals from the first light receiving part; and an arithmetic part for obtaining the optical characteristic of the subject eye by combining the first signals obtained from the first light receiving part under the plural measurement conditions in a process of adjustment of the adjustment part.

BRIEF DESCRIPTION OF THE DRAWINGS

FIG. 1 is a view schematically showing an optical system of an ophthalmic measuring apparatus of the invention.

FIGS. 5A and 5B are explanatory views of an influence on a Hartmann image due to the positional shift at the projection side and the light receiving side.

FIGS. 6A and 6B are views showing Hartmann images at the time of occurrence of the positional shift at the projection side.

FIGS. 7A and 7B are views showing Hartmann images at the time of occurrence of the positional shift at the light receiving side.

FIGS. 8A and 8B are views showing point images measured in a case where there is a large difference in the distribution of an eye characteristic.

FIGS. 9A and 9B are views showing a memory format of measurement data and inference data.

FIG. 17 shows Zernike polynomials (1).

FIG. 18 shows Zernike polynomials (2).

DETAILED DESCRIPTION OF THE INVENTION

Figure 2:
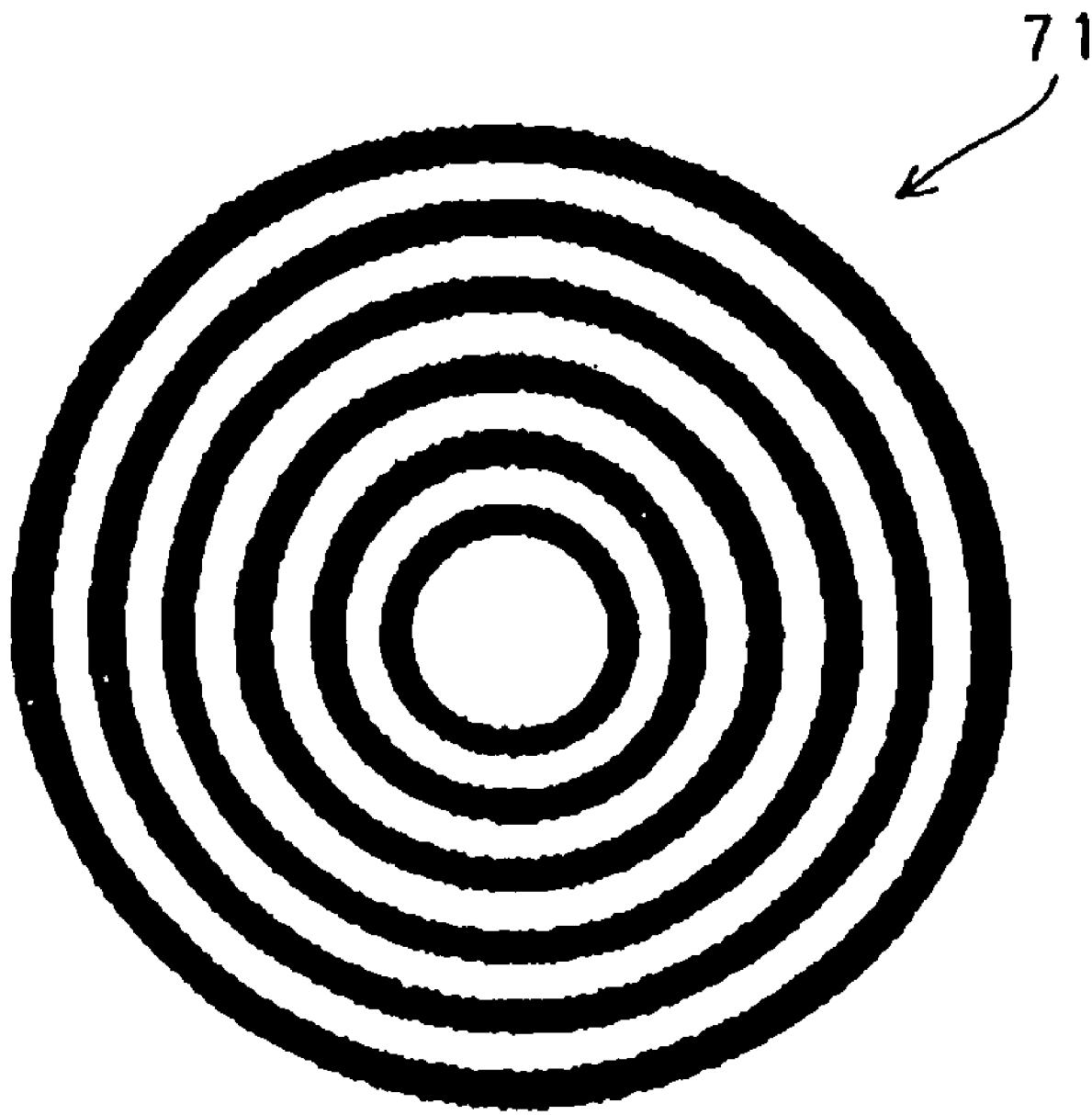
FIG. 2 is a structural view of a Placido's disc.

Hereinafter, an embodiment of the invention will be described in detail with reference to the drawings.

1. Structure of an Ophthalmic Measuring Apparatus

Figure 1:
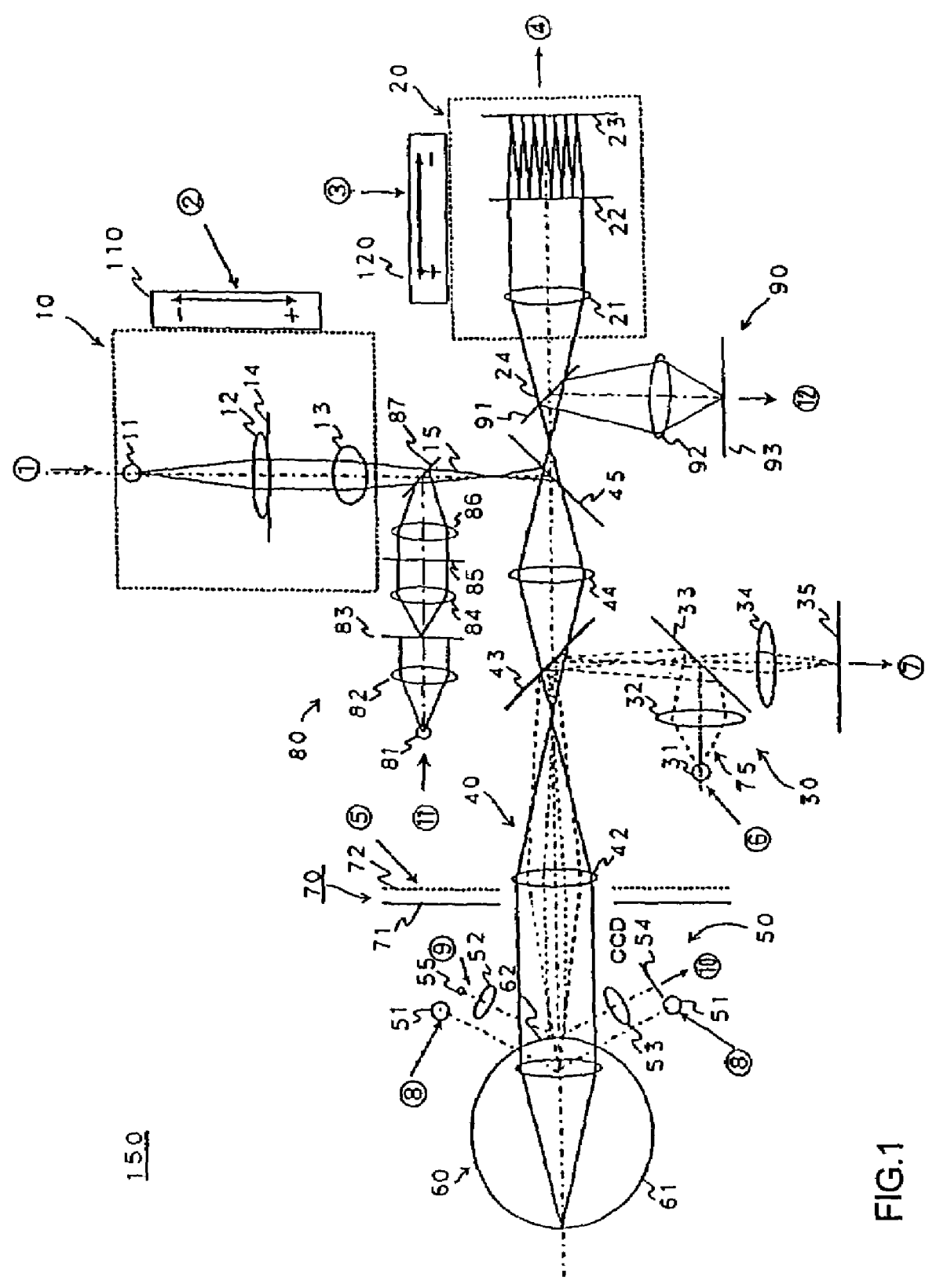

FIG. 1 is a view schematically showing an optical system 150 of an ophthalmic measuring apparatus of the invention.

The optical system 150 of the ophthalmic measuring apparatus is, for example, an apparatus for measuring an optical characteristic of a subject eye 60 as an object, and includes a first illumination optical system 10, a first light receiving optical system 20, a second light receiving optical system 30, a common optical system 40, an adjusting optical system 50, a second illumination optical system 70, a third illumination optical system 75, an illumination optical system 80 for refraction measurement, a light receiving optical system 90 for refraction measurement, first movement means 110, and second movement means 120. Incidentally, with respect to the subject eye 60, a retina 61 and a corneal 62 are shown in the drawing.

The first illuminating optical system 10 includes, for example, a first light source 11 for emitting a light flux of a first wavelength, and a condensing lens 12, and is for illuminating a minute region on the retina (fundus) 61 of the subject eye 60 with the light flux (first illumination light flux) from the first light source 11 so that its illumination condition can be suitably set. The first illuminating optical system 10 can move a condensing position and/or change a condensing condition by the first movement means 110.

The first wavelength of the first illumination light flux emitted from the first light source 11 is, as an example, a wavelength in an infrared range (for example, 780 nm). It is desirable that the first light source 11 has a large spatial coherence and a small temporal coherence. Here, the first light source 11 is, for example, a super luminescence diode (SLD), and a point light source having high luminescence can be obtained. Incidentally, the first light source 11 is not limited to the SLD, and for example, a laser having a large spatial coherence and a large temporal coherence can also be used by inserting a rotation diffused plate or the like to suitably lower the temporal coherence. Further, an LED having a small spatial coherence and a small temporal coherence can also be used, if light quantity is sufficient, by inserting, for example, a pinhole or the like at a position of a light source in an optical path.

The first light receiving optical system 20 includes, for example, a collimator lens 21, a Hartmann plate 22 as a conversion member for converting part of a light flux (first light flux) reflected and returned from the retina 61 of the subject eye 60 into at least 17 beams, and a first light receiving part 23 for receiving the plural beams converted by this Hartmann plate 22, and is for guiding the first light flux to the first light receiving part 23. The first light receiving optical system 20 can be moved by the second movement means 120 so that the beams converted by the Hartmann plate 22 are condensed on the first light receiving part 23. Besides, here, a CCD with little readout noise is adopted for the first light receiving part 23, and as the CCD, a suitable type of CCD, for example, a general low noise type of CCD, or a cooling CCD of 1000×1000 elements for measurement, can be applied. Signals (first received light signals) received by the first light receiving part 23 are used for obtaining, for example, ocular higher order aberrations.

The first movement means 110 is for moving the first illuminating optical system, and is driven by, for example, a motor. The condensing position of the first illumination light flux from the first illuminating optical system can be adjusted by moving the first illuminating optical system by the first movement means 110.

The second movement means 120 is for moving the first light receiving optical system, and is driven by, for example, a motor. By moving the first light receiving optical system by the second movement means 120, an adjustment can be made such that the beams converted by the Hartmann plate 22 are condensed on the first light receiving part 23. Incidentally, a suitable apparatus and method can be used as the movement means of the first movement means 110 and the second movement means 120. Besides, in this embodiment, the first movement means 110 and the second movement means 120 can be driven together, and besides, they can be driven independently. Incidentally, in addition of the automatic measurement by these movement means, the first movement means 110 and the second movement means 120 may be enable to drive by the operation (manual operation) of an operator.

The second illuminating optical system 70 includes a second light source 72 for emitting a light flux of a second wavelength, and a Placido's disk 71. Incidentally, the second light source 72 can be omitted. FIG. 2 shows an example of a structural view of the Placido's disk 71. The Placido's disk (PLACIDO'S DISK) 71 is for projecting an index of a pattern composed of plural co-axial rings as shown in FIG. 2. Incidentally, the index of the pattern composed of the plural co-axial rings is an example of an index of a predetermined pattern, and a different suitable pattern can be used. Then, after an alignment adjustment described later is completed, the index of the pattern composed of the plural co-axial rings can be projected.

The third illuminating optical system 75 is for mainly performing, for example, the alignment adjustment described later, and includes a third light source 31 for emitting a light flux of a third wavelength, a condensing lens 32, and a beam splitter 33.

The second light receiving optical system 30 includes a condensing lens 34 and a second light receiving part 35. The second light receiving optical system 30 guides a light flux (second light flux), in which the pattern of the Placido's disk 71 illuminated from the second illuminating optical system 70 is reflected and returned from the anterior part or the cornea 62 of the subject eye 60, to the second light receiving part 35. Besides, the second light receiving optical system can guide a light flux (third light flux), which is emitted from the third light source 31 and is reflected and returned from the cornea 62 of the subject eye 60, to the second light receiving part 35. Besides, the second light receiving optical system can obtain the anterior eye image illuminated by the fourth light source 51 from the second light receiving part 35. Incidentally, as the second wavelength and the third wavelength of the light fluxes emitted from the second light source 72 and the third light source 31, a wavelength different from, for example, the first wavelength (here, 780 nm) and long (for example, 940 nm) can be selected. Besides, the signal received by the second light receiving part 35 is used for, for example, the alignment adjustment or for obtaining corneal higher order aberrations.

The common optical system 40 is disposed on an optical axis of the light flux emitted from the first illuminating optical system 10, can be included in the first and the second illuminating optical systems 10 and 70, the first and the second light receiving optical systems 20 and 30, the third illuminating optical system 75, and the like, and includes, for example, an afocal lens 42, beam splitters 43 and 45, and a condensing lens 44. The beam splitter 43 is formed of such a mirror (for example, a dichroic mirror) that the wavelength of the third light source 31 is sent (reflected) to the subject eye 60, the second light flux and the third light flux reflected and returned from the cornea 62 of the subject eye 60 are reflected, and the wavelength of the first light source 11 is transmitted. The beam splitter 45 is formed of such a mirror (for example, a polarization beam splitter) that the wavelength of the first light source 11 is sent (reflected) to the subject eye 60, and the first light flux reflected and returned from the retina 61 of the subject eye 60 is transmitted. By the beam splitters 43 and 45, the first, the second and the third light fluxes do not mutually enter other optical systems to generate noise.

The adjusting optical system 50 is for mainly performing, for example, an operation distance adjustment, and includes, a fifth light source 55, condensing lenses 52 and 53, and a third light receiving part 54. The operation distance adjustment is performed in such a way that for example, a parallel light flux in the vicinity of an optical axis emitted from the fifth light source 55 is irradiated to the subject eye 60, and the light reflected from this subject eye 60 is received by the third light receiving part 54 through the condensing lenses 52 and 53. Besides, in the case where the subject eye 60 is in a suitable operation distance, a spot image from the fifth light source 55 is formed on the optical axis of the third light receiving part 54. On the other hand, in the case where the subject eye 60 is not within the suitable operation distance, a spot image from the fifth light source 55 is formed above or below the optical axis of the third light receiving part 54. Incidentally, since the third light receiving part 54 has only to detect the change of a light flux position on the plane including the fifth light source 55, the optical axis, and the third light receiving part 54, for example, a one-dimensional CCD, a position selecting device (PSD) or the like disposed on this plane can be applied.

The illumination optical system 80 for the refraction measurement includes a light source 81 for refraction measurement, a collimate lens 82, a ring-shaped diaphragm 83 for refraction measurement, a relay lens 84, a ring-shaped diaphragm 85, and a beam splitter 87. An illumination light flux emitted from the light source 81 for the refraction measurement becomes a parallel light flux by the collimate lens 82, and illuminates the ring-shaped pattern 83 for the refraction measurement. A light flux from the illuminated ring-shaped diaphragm 83 for the refraction measurement becomes parallel by the relay lens 84, passes through the ring-shaped diaphragm 85 conjugate with a pupil and the relay lens 86, overlaps with an optical axis of the first illumination optical system 10 through the beam splitter 87, and illuminates the retina 61 of the subject eye 60 through the common optical system 40. This ring-shaped diaphragm 83 for the refraction measurement is made to have a conjugate positional relation to the retina of the subject eye at the time of measurement of the orthoscopic subject eye.

The light receiving optical system 90 for refractive power measurement includes a beam splitter 91, a relay lens 92, and a light receiving part 93 for refractive power measurement. A reflected light flux from the retina 61 of the ring-illuminated subject eye 60 reaches the beam splitter 91 through the common optical system 40, is reflected here, and after being condensed by the relay lens 92, the light flux is received as a received light signal for refractive power measurement by the light receiving part 93 for refractive power measurement. The received light signal for refractive power measurement indicating the ring-shaped pattern image for refractive power measurement projected on the retina is sent to the arithmetic part 210.

The light receiving part 93 for refractive power measurement is preferably formed of a two-dimensional sensor. The arithmetic part 210 obtains the refractive power of the subject eye 60 on the basis of the received light signal for refractive power measurement and from the ring-shaped pattern image for refractive power measurement projected on the retina.

Next, the alignment adjustment will be described. The alignment adjustment is mainly carried out by the second light receiving optical system 30 and the third illuminating optical system 75.

First, the light flux from the third light source 31 illuminates the subject eye 60 as the object with the parallel light flux through the condensing lens 32, the beam splitters 33 and 43, and the afocal lens 42. The reflected light flux reflected by the cornea 62 of the subject eye 60 is emitted as a divergent light flux such as is emitted from a point of the half of the radius of curvature of the cornea 62. The divergence light flux is received as the spot image by the second light receiving part 35 through the afocal lens 42, the beam splitters 43 and 33, and the condensing lens 34.

Here, in the case where the spot image on the second light receiving part 35 is out of the optical axis, the optical characteristic measuring apparatus body is moved and adjusted vertically and horizontally, and the spot image is made to coincide with the optical axis. As stated above, when the spot image coincides with the optical axis, the alignment adjustment is completed. Incidentally, with respect to the alignment adjustment, the cornea 62 of the subject eye 60 is illuminated with the fourth light source 51, and the image of the subject eye 60 obtained by this illumination is formed on the second light receiving part 35, and accordingly, the center of the pupil may be made to coincide with the optical axis by using this image.

Next, a positional relation between the first illuminating optical system 10 and the first light receiving optical system 20 will be roughly described.

The beam splitter 45 is inserted in the first light receiving optical system 20, and by this beam splitter 45, the light from the first illuminating optical system 10 is sent to the subject eye 60, and the reflected light from the subject eye 60 is transmitted. The first light receiving part 23 included in the first light receiving optical system 20 receives the light transmitted through the Hartmann plate 22 as the conversion member and generates the received light signal.

Besides, the first light source 11 and the retina 61 of the subject eye 60 form a conjugated relation. The retina 61 of the subject eye 60 and the first light receiving part 23 are conjugate. Besides, the Hartmann plate 22 and the pupil of the subject eye 60 form a conjugated relation. Further, in the first light receiving optical system 20, the pupil and the Hartmann plate 22 form substantially the conjugated relation. That is, the front focal point of the afocal lens 42 substantially coincides with the pupil.

Besides, the lens 12 converts a diffused light of the light source 11 into a parallel light. A diaphragm 14 is positioned at an optically conjugated position with respect to the pupil of the eye and the Hartmann plate 21. The diaphragm 14 has a diameter smaller than an effective range of the Hartmann plate 21, and the so-called single path aberration measurement (method in which the aberration of an eye influences on only the light receiving side) is established. In order to satisfy the above, the lens 13 is disposed such that the conjugated point of the retina of the real light beam coincides with the front focal position, and in order to satisfy the conjugated relation between the lens and the pupil of the eye, it is disposed such that the rear focal position coincides with the diaphragm 14.

Besides, after a light beam 15 comes to have a light path common to a light beam 24 by the beam splitter 45, it travels in the same way as the light beam 24 paraxially. However, at the single path measurement, the diameters of the light beams are different from each other, and the beam diameter of the light beam 15 is set to be rather small as compared with the light beam 24. Specifically, the beam diameter of the light beam 15 is about 1 mm at the pupil position of the eye, and the beam diameter of the light beam 24 can be about 7 mm (incidentally, in the drawing, the light beam 15 from the beam splitter 45 to the retina 61 is omitted).

Next, the Hartmann plate 22 as the conversion member will be described.

The Hartmann plate 22 included in the first light receiving optical system 20 is a wavefront conversion member for converting a reflected light flux into plural beams. Here, plural micro-Fresnel lenses disposed on a plane orthogonal to the optical axis are applied to the Hartmann plate 22. Besides, in general, with respect to a measurement object part (subject eye 60), in order to measure a spherical component of the subject eye 60, a third order astigmatism, and other higher order aberrations, it is necessary to perform the measurement with at least 17 beams through the subject eye 60.

Besides, the micro-Fresnel lens is an optical element, and includes, for example, a ring of a height pitch for each wavelength, and a blade optimized for emission parallel to a condensing point. The micro-Fresnel lens here is subjected to, for example, optical path length difference of 8 levels applied by a semiconductor fine working technique, and achieves a high condensing efficiency (for example, 98%).

Besides, the reflected light from the retina 61 of the subject eye 60 passes through the afocal lens 42, the collimate lens 21, and is condensed on the first light receiving part 23 through the Hartmann plate 22. Accordingly, the Hartmann plate 22 includes a wavefront conversion member for converting the reflected light flux into at least 17 beams.

Figure 3:
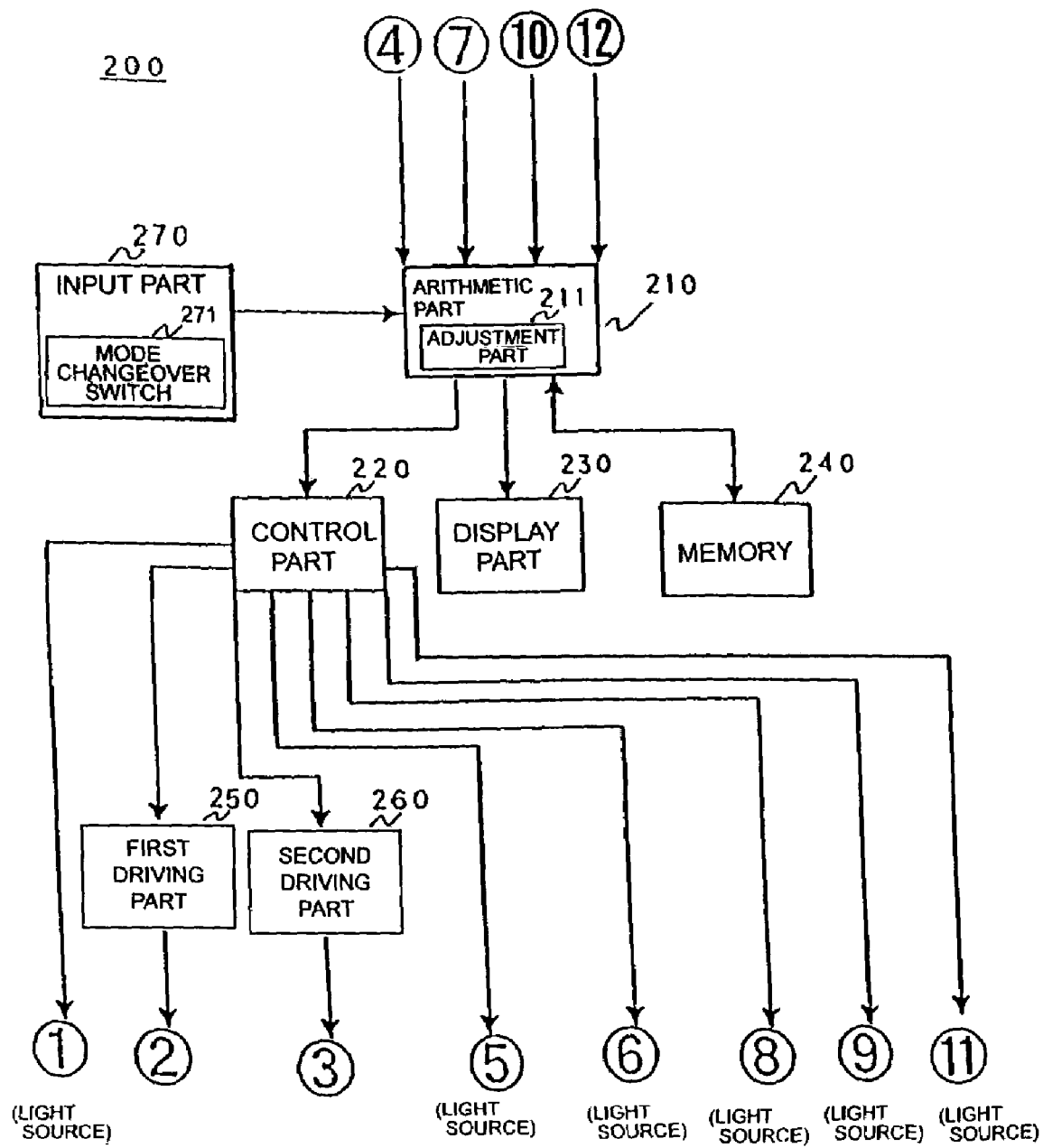
FIG. 3 is a block diagram schematically showing an electric system of the ophthalmic measuring apparatus of the invention.

FIG. 3 is a block diagram roughly showing an electrical system 200 of the ophthalmic measuring apparatus of the invention. The electrical system 200 of the ophthalmic measuring apparatus includes, for example, an arithmetic part 210, a control part 220, a display part 230, a memory 240, a first driving part 250, a second driving part 260, and an input part 270.

The arithmetic part 210 receives a light receiving signal ④ obtained from the first light receiving part 23, a light receiving signal ⑦ obtained from the second light receiving part 35, a light receiving signal ⑩ obtained from the third light receiving part 54, and a light receiving signal ⑫ obtained from the light receiving part 93 for the refraction measurement, and performs arithmetic operations on an ocular aberration, Zernike coefficients, refraction and the like. Further, the arithmetic part 210 receives input signals of desired setting, instructions, data and the like from the input part 270. Besides, the arithmetic part 210 performs arithmetic operations on corneal higher order aberrations, aberration coefficients, a white light MTF (Modulation Transfer Function) as an index expressing a transmission characteristic of a spatial frequency, a Strehl ratio obtained by dividing the center intensity of an intensity distribution PSF (Point Spread Function) of point images by the center intensity of the PSF obtained in the case of an aberration free optical system, a Landolt's ring pattern having a size corresponding to suitable visual acuity to examine the visual acuity of a patient, and the like. Besides, the arithmetic part outputs signals corresponding to such arithmetic operation results to the control part 220 for performing the control of the whole electric driving system, the display part 230 and the memory 240, respectively.

Further, the arithmetic part 210 includes an adjustment part 211. The adjustment part 211 adjusts the positions of the first illumination optical system 10 and the first light receiving optical system 20 by the first and the second movement means 110 and 120 so that measurable Hartmann images are obtained.

On the basis of the control signal from the arithmetic part 210, the control part 220 performs a control to turn on and off the first light source part 11 and the optical source 81 for the refraction measurement, and controls the first driving part 250 and the second driving part 260. For example, on the basis the signals corresponding to the operation results in the arithmetic part 210, the control part outputs a signal ① to the first light source part 11, outputs a signal ⑤ to the Placido's disk 71, outputs a signal ⑥ to the third light source part 31, outputs a signal ⑧ to the fourth light source part 51, outputs a signal ⑨ to the fifth light source part 55, outputs a signal ⑪ to the light source 81 for the refraction measurement, and outputs signals to the first driving part 250 and the second driving part 260.

The first driving part 250 moves the whole of the first illumination optical system 10 in an optical axis direction on the basis of the light receiving signal ④ inputted to the arithmetic part 210 from the first light receiving part 23 or the movement signal inputted from input part 270 so that the light condensing position is moved and/or the light condensing state is changed, and outputs a signal ② to the first movement means 110 and drives this movement means. By this, the first driving part 250 can move and adjust the first illumination optical system 10.

The second driving part 260 moves the whole of the first light receiving optical system 20 in the optical axis direction on the basis of the light receiving signal ④ inputted to the arithmetic part 210 from the first light receiving part 23 or the input signal inputted from the input part 270, and outputs a signal ③ to the second movement means 120 and drives this movement means. By this, the second driving part 260 can move and adjust the first light receiving optical system 20.

The input part 270 includes a switch, a button, a keyboard, a pointing device and the like for inputting various input signals of desired setting, instructions, data and the like. For example, the input part 270 includes a mode changeover switch 271. The mode changeover switch 271 is a switch for switching between an interlock mode in which the first illumination optical system 10 and the first light receiving optical system 20 are interlocked and moved and an independent mode in which they are independently moved. Besides, the input part may include an operation changeover switch for switching between measurement by an automatic adjustment and measurement by a manual adjustment, a measurement start button, and a movement switch for moving the first illumination optical system 10 or the first light receiving optical system 20 in a+ direction and a− direction.

Next, a Zernike analysis will be described. A method of calculating Zernike coefficients $C_i^{2j-i}$ from a generally known Zernike polynomial expression will be described. The Zernike coefficients $C_i^{2j-i}$ are an important parameter for grasping the optical characteristic of the subject eye 60 on the basis of tilt angles of light fluxes obtained by the first light receiving part 23 through the Hartmann plate 22.

A wavefront aberrations W(X, Y) of the subject eye 60 is expressed by the following expression using the Zernike coefficients $C_i^{2j-i}$ and the Zernike polynomial expression $Z_i^{2j-i}$.

$$W(X, Y) = \sum_{i=0}^{n} \sum_{j=0}^{i} c_i^{2j-i} Z_i^{2j-i}(X, Y) \quad \text{[Numerical Expression 1]}$$

Where, (X, Y) denotes vertical and horizontal coordinates of the Hartmann plate 22. Besides, in the above expression, n denotes an analysis order.

Besides, with respect to the wavefront aberrations W(X, Y), when the vertical and horizontal coordinates of the first light receiving part 23 is (x, y), the distance between the Hartmann plate 22 and the first light receiving part 23 is f, and the movement distance of a point image received by the first light receiving part 23 is ($\Delta x$, $\Delta y$), the relation of the following expression is established.

$$\frac{\partial W(X, Y)}{\partial X} = \frac{\Delta x}{f} \quad \text{[Numerical Expression 2]}$$

$$\frac{\partial W(X, Y)}{\partial Y} = \frac{\Delta y}{f}$$

Here, the Zernike polynomial expression $Z_n^m$ is expressed by the following numerical expression 3, and is specifically shown in FIGS. 17 and 18. Where, n and m correspond to i and 2j-i in FIGS. 17 and 18.

$$Z_n^m = R_n^m(r) \begin{Bmatrix} \sin \\ \cos \end{Bmatrix} \{m\theta\} \quad \text{[Numerical Expression 3]}$$

$$m > 0 \quad \sin$$
$$m \leq 0 \quad \cos$$

$$R_n^m(r) = \sum_{S=0}^{(n-m)/2} (-1)^S \frac{(n-S)!}{S! \left\{\frac{1}{2}(n-m) - S\right\}! \left\{\frac{1}{2}(n+m) - S\right\}!} r^m$$

Incidentally, specific values of the Zernike coefficients $C_i^{2j-i}$ can be obtained by minimizing a square error expressed by following numerical expression 4.

$$S(x) = \sum_{i=1}^{data\ number} \left[ \left\{ \frac{\partial W(X_i, Y_i)}{\partial X} - \frac{\Delta x_i}{f} \right\}^2 + \left\{ \frac{\partial W(X_i, Y_i)}{\partial Y} - \frac{\Delta y_i}{f} \right\}^2 \right] \quad \text{[Numerical Expression 4]}$$

Where, W(X, Y): wavefront aberrations, (X, Y): Hartmann plate coordinates, ($\Delta x$, $\Delta y$): movement distance of the point image received by the first light receiving part 23, and f: distance between the Hartmann plate 22 and the first light receiving part 23.

The arithmetic part 210 calculates the Zernike coefficients $C_i^{2j-i}$, and uses these to obtain the optical characteristic of the eye, such as spherical aberrations, coma aberrations, and astigmatic aberrations.

2. Influence of Positional Deviation of the Illuminating Optical System and the Light Receiving Optical System Next, a description will be given of an influence on a Hartmann image in a case where diopter values of the first illuminating optical system 10 (projection side) and the first light receiving optical system 20 (light receiving side) are deviated.

Figure 4:
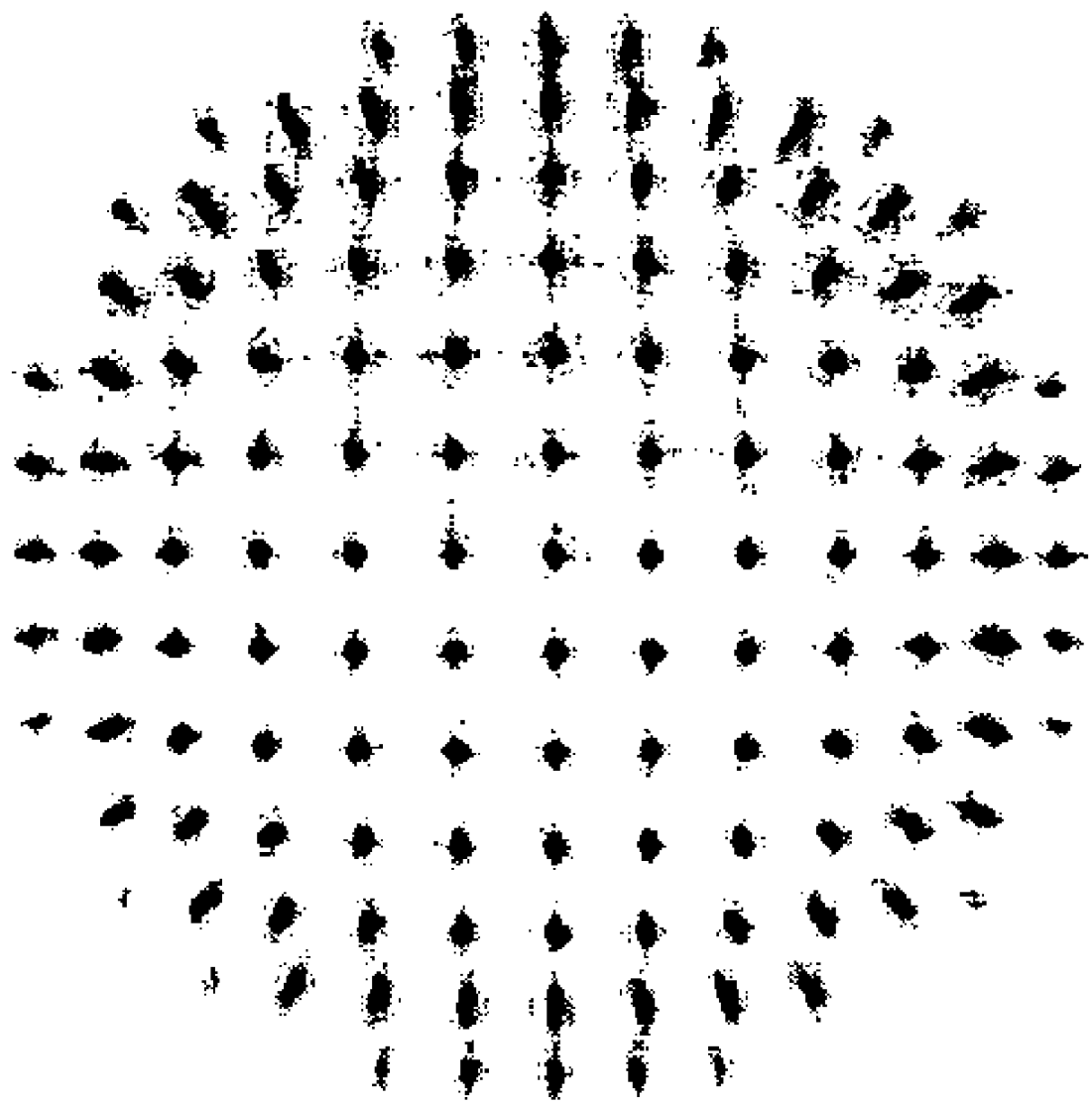
FIG. 4 is a view showing a Hartmann image in a case where there is no positional shift at a projection side and a light receiving side.

FIG. 4 is a view of a Hartmann image in the case where there is no positional deviation at the projection side and the light receiving side. The drawing shows the Hartmann image in the case where a light flux emitted from the first illuminating optical system 10 is reflected by the retina 61 of the subject eye 60 and is condensed on the first light receiving part 23, that is, in the case where there is no positional deviation at the projection side and the light receiving side.

FIGS. 5A and 5B are explanatory views each showing an influence on the Hartmann image due to positional deviation of the projection side or the light receiving side. Hereinafter, with reference to FIGS. 5A and 5B, the Hartmann images shown in FIGS. 6A and 6B and FIGS. 7A and 7B will be described.

FIGS. 6A and 6B are views each showing the Hartmann image at the time of the occurrence of positional deviation of the projection side. FIG. 6A shows the Hartmann image in the case where only the projection side is deviated from the state of FIG. 4 by +5 diopters (+5D). When the projection side is deviated in the+ direction, as indicated by a broken line of FIG. 5A, since the light flux emitted from the first illuminating optical system 10 is incident from the outside of the center axis toward the inside direction, it is condensed in front of the retina 61 of the subject eye 60. Since the light flux not condensed is reflected by the retina 61, when the reflected light flux is received by the first light receiving part 23, the point image of a received light signal becomes blurred, and the received light level (light quantity) of the received light signal becomes low.

On the other hand, FIG. 6B shows the Hartmann image in the case where only the projection side is deviated from the state of FIG. 4 by −5 diopters (−5D). When the projection side is deviated in the− direction, as indicated by a solid line of FIG. 5A, since the light flux emitted from the first illuminating optical system 10 is incident from the inside of the center axis toward the outside direction, the light flux is condensed at the rear of the retina 61 of the subject eye 60. Similarly to the case where the projection side is deviated in the+ direction, since the light flux not condensed is reflected by the retina 61, when the reflected light flux is received by the first light receiving part 23, the point image of a received light signal becomes blurred, and the received light level of the received light signal becomes low.

As stated above, the projection side relates to the received light level of the point image of the received light signal received by the first light receiving part 23. That is, when the projection side is moved, the point image can be blurred or sharpened. In order to enhance the received light level, the projection side is moved in one of the+ direction and the− direction in which the received light level becomes large. In the automatic adjustment, the arithmetic part 210 moves the first illuminating optical system 10 on the basis of the received light signal of the first light receiving part 23 so that the received light level of the point image becomes large, and the diopter value of the projection side is adjusted.

FIGS. 7A and 7B are views each showing a Hartmann image at the time of the occurrence of positional deviation at the light receiving side. FIG. 7A shows the Hartmann image in the case where only the light receiving side is deviated from the state of FIG. 4 by +5D. When the light receiving side is deviated in the+ direction, as indicated by a broken line of FIG. 5B, since a light flux reflected by the retina 61 is incident on the Hartmann plate 22 from the outside of the center axis toward the inside direction, not in the vertical direction, it is condensed on a place closer to the center axis, and reaches the first light receiving part. The point images received by the first light receiving part 23 are collected in a place closer to the center axis on the whole, and become, as shown in FIG. 7A, images in which point image intervals are small.

On the other hand, FIG. 7B shows the Hartmann image in the case where only the light receiving side is deviated from the state of FIG. 4 by −5D. When the light receiving side is deviated in the− direction, as indicated by a solid line of FIG. 5B, the light flux reflected by the retina 61 is incident on the Hartmann plate 22 from the inside of the center axis toward the outside direction, not in the vertical direction, and it is condensed apart from the center axis. The point images received by the first light receiving part 23 go away from the center axis on the whole, and become images as shown in FIG. 7B in which point image intervals are large.

As stated above, the light receiving side relates to the point image intervals of the point images of the light receiving signals received by the first light receiving part 23. That is, the correction to a suitable diopter value can be performed by moving the light receiving side in the− direction in the case where the point image interval is small, and by moving the light receiving side in the+ direction in the case where the point image interval is large. In the automatic adjustment, on the basis of the light receiving signal of the first light receiving part 23, the arithmetic part 210 moves the first light receiving optical system side so that the point image interval becomes a predetermined interval, and as a result, the diopter value of the light receiving side is adjusted. Incidentally, in this embodiment, the first illumination optical system 10 and the first light receiving optical system 20 can be independently moved, and the point image level and the point image interval can be independently adjusted.

FIGS. 8A and 8B are views showing an example of point images measured in the case where there is a large difference in the distribution of an eye characteristic, such as a refractive index, refraction or aberration, of an eye. FIG. 8A shows an example in which at the first measurement, although an area near the center is a measurable area, the peripheral portion is an unmeasurable area. In such a case, the adjustment part 211 makes an adjustment so that the unmeasurable area becomes the measurable area. FIG. 8B is a view in which the first light receiving optical system 20 is moved in the− direction, and shows that although the center part becomes the unmeasurable area, the peripheral part can be detected as the measurable area. As a result, the total measurement becomes possible by combining data of the center part of FIG. 8A and data of the peripheral part of FIG. 8B.

3. Data Format

FIGS. 9A and 9B show memory formats of measurement data and inference data stored in the memory 240. FIG. 9A shows the memory format of the measurement data, and for example, a measurement condition and a measurement result are stored correspondingly to a data identifier to identify data measured under plural measurement conditions. The measurement condition includes diopter values (D values) corresponding to the positions of the first illumination optical system 10 (projection side) and the first light receiving optical system 20 (light receiving side) adjusted by the adjustment part 211. Besides, for example, measurable identification information corresponding to respective area identifiers related to respective areas of the Hartmann image divided into plural parts and indicating whether the respective areas are measurable areas judged by the arithmetic part 210 or unmeasurable areas, and measurement values (for example, point image coordinates) based on the signals from the first light receiving part 23 are stored in the measurement result.

FIG. 9B shows the recording format of the inference data, and for example, an inference result and the like are stored correspondingly to a data identifier. The inference result includes measurable identification information corresponding to the area identifiers, and inference values (for example, point image coordinates) which suggest results of cases where measurements are made under conditions different from the measurement conditions and are inferred on the basis of the measurement values. Incidentally, as the data identifiers and the area identifiers, suitable ones of numerals, characters, symbols and the like can be used. Besides, these data formats can take suitable forms.

4. Flowchart

Figure 10:
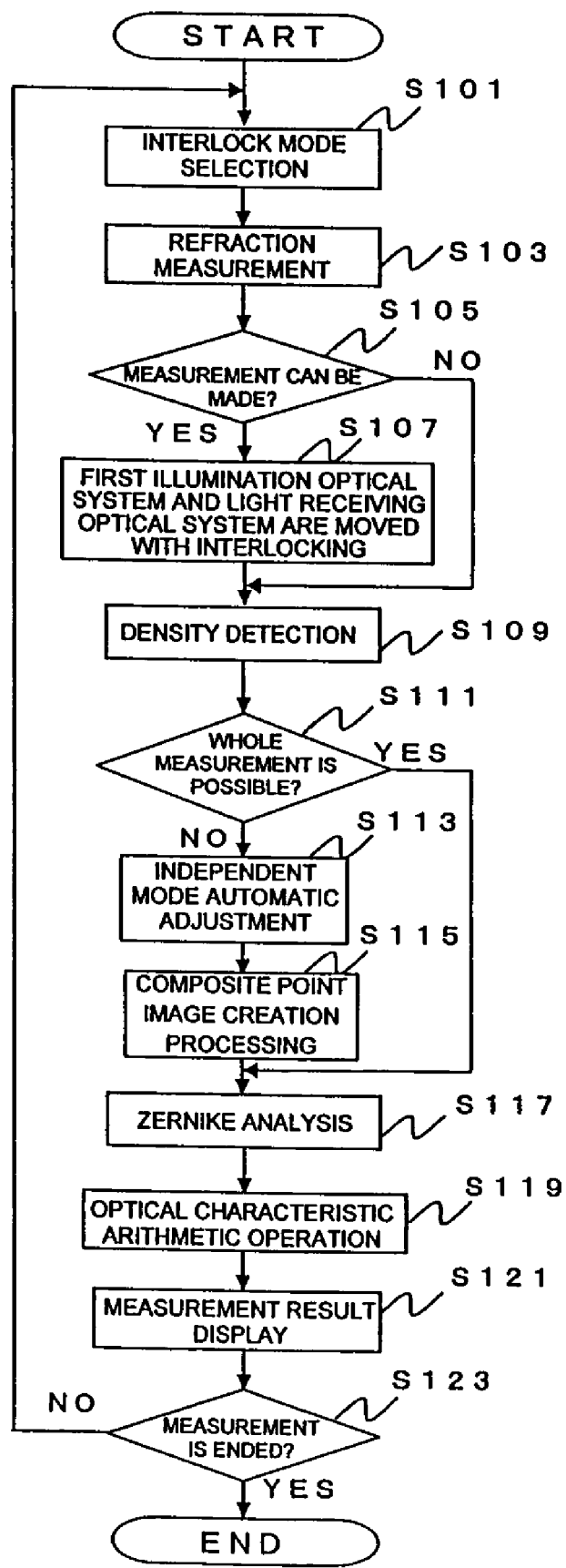
FIG. 10 is a flowchart for obtaining an optical characteristic of a subject eye by combining Hartmann images.

FIG. 10 shows a flowchart for obtaining the optical characteristic of the subject eye 60 by combining plural Hartmann images.

First, in the case of the preset interlock mode, the arithmetic part 210 selects the interlock mode in which the first illumination optical system 10 and the first light receiving optical system 20 are interlocked and moved, and makes an alignment adjustment (S101).

Next, the arithmetic part 210 illuminates the retina 62 of the subject eye 60 with the ring-shaped pattern 83 for the refraction measurement through the illumination optical system 80 for the refraction measurement, receives the reflected light flux reflected from the retina 62 by the light receiving part 93 for the refraction measurement, and obtains the refraction of the subject eye 60 on the basis of the received light receiving signal for the refraction measurement (S103). Since an arithmetic operation for obtaining the refraction is disclosed in Japanese Patent No. 2580215 (patent document 2), the details will be omitted here.

The arithmetic part 210 judges whether the measurement result of the refraction is obtained (S105). The arithmetic part 210 may judge whether the measurement result of the refraction is obtained by using a condition, for example, whether a predetermined number of data necessary for the arithmetic operation of the refraction are obtained. Incidentally, a suitable condition can be used in addition to this. In the case where the refraction measurement result is obtained (S105), the arithmetic part 210 interlocks and moves the first illumination optical system 10 and the first light receiving optical system 20 to a position consistent with the refractive power component of the obtained refraction (S107). On the other hand, when the refraction measurement result is not obtained (S105), the arithmetic part 210 proceeds to step S109. Incidentally, in the case where the refraction measurement result is not obtained, the arithmetic part 210 may proceed to an independent mode automatic adjustment of step S113.

Next, the arithmetic part 210 receives the first light receiving signal from the first light receiving part 23, and detects the density distribution of point images on the basis of the received first light receiving signal (S109). For example, a range of the first light receiving part 23, which can receive light, is previously divided into a suitable number of areas, the arithmetic part 210 judges the point images existing in the respective areas from the coordinates or the like of the first light receiving signal, and may detect the number thereof to obtain the point image density. Incidentally, with respect to the calculation of the density, a suitable method can be adopted.

Besides, in addition to the use of the previously divided areas, the arithmetic part 210 may perform division of areas in accordance with the first light receiving signal from the first light receiving part 23. For example, the arithmetic part 210 detects point image coordinates of vertical and horizontal ends from the first light receiving signal, and obtains the distribution range of the point images, and this distribution range can also be divided into a suitable number of parts. As a dividing method, a suitable method and a suitable number of divided parts, for example, a method in which the vertical width is divided into four parts, the horizontal width is divided into four parts, and the whole is divided into 16 parts, or a method of dividing the range into concentric areas having the center of the distribution range as the center can be adopted. The divided areas are made to correspond to area identifiers such as area numbers. Incidentally, as the area identifiers, suitable ones such as numerals, characters, or symbols can be used.

The arithmetic part 210 reads out a predetermined range of a previously set density from the memory 240, and judges that it is an unmeasurable area when the density of the point images of each area is outside a predetermined range, and judges that it is a measurable area when the density is within the predetermined range. The predetermined range is, for example, d1/10 or higher and 5×d1 or less when the density of the point images in the case where the orthoscopic subject eye 60 is measured at a position of 0 diopter (0 D) is made d1. Incidentally, as the predetermined range, a suitable range may be used in addition to this. Besides, in addition to the judgment of the measurable areas on the basis of the point image density, the arithmetic part 210 may judge the measurable areas on the basis of the maximum value of the point images. In this case, the arithmetic part 210 obtains the maximum value of the respective point image levels on the basis of the first light receiving signal, and reads out a predetermined range of previously set point image levels from the memory 240, and in the case where the maximum value of the point image levels is within the predetermined range, it is judged to be the measurable area, and in the case where the maximum value is outside the predetermined range, it is judged to be the unmeasurable area.

Besides, the arithmetic part 210 can store diopter values (measurement condition) consistent with the positions of the first illumination optical system 10 and the first light receiving optical system 20 when the first light receiving signal is received, and the coordinates (measurement value) of point images on the basis of the inputted first light receiving signal, which are made to correspond to the data identifier (for example, data number), into the measurement data of the memory 240 at a suitable timing. Incidentally, the arithmetic part 210 may store the measurement value which is made to correspond to the area identifier for each area. Further, the arithmetic part 210 can store the measurable identification information indicating measurability or unmeasurability, which is made to correspond to the pertinent area identifier, into the memory 240.

The arithmetic part 210 judges whether the whole light receivable range of the first light receiving part 23 is a measurable area (S111). That is, on the basis of the judgment at the step S109 as to whether each area is the measurable area or on the basis of the measurable identification information of the measurement data stored in the memory 240, when the arithmetic part 210 judges that the whole light receivable range is covered with the measurable area, it proceeds to step S117 and obtains the optical characteristic of the subject eye 60. On the other hand, when judging that the whole is not covered with the measurable area, the arithmetic part 210 proceeds to step S113. Incidentally, as a judgment condition, instead of judging whether the whole is the measurable area, the arithmetic part 210 may judge, for example, whether the number of obtained point images is a predetermined number or larger. In that case, in the case where the number of the point images is the predetermined number or larger, the arithmetic part proceeds to the step S117, and in the case where the number of the point images is smaller than the predetermined number, it proceeds to the step S113. Further, as a judgment condition, the arithmetic part 210 may judge whether the point image density is within a predetermined range and whether the number of point images is a predetermined number or larger.

The arithmetic part 210 performs an independent mode automatic adjustment processing (S113). In the independent mode automatic adjustment processing, the arithmetic part 210 adjusts the first illumination optical system 10 and the first light receiving optical system 20 on the basis of the point images of the unmeasurable area, and acquires Hartmann images necessary for measurement. The detailed description of the independent mode automatic adjustment processing will be described later.

Besides, the arithmetic part 210 performs a composite point image creation processing for obtaining a composite point image on the basis of one or plural first light receiving signals captured (S115). The arithmetic part 210 performs a Zernike analysis on the basis of the first light receiving signal or the composite point image, and calculates Zernike coefficients (S117).

Next, the arithmetic part 210 performs an arithmetic processing on the optical characteristic on the basis of the first light receiving signal (S119). Here, the optical characteristic is a suitable eye characteristic, for example, aberrations or eye refraction. The arithmetic part 210 calculates the optical characteristic based on the measurement principle of a Hartmann wavefront sensor with respect to the first light receiving signal. Higher order aberrations (ocular higher order aberrations) of an ocular optical system are obtained by the first light receiving signal. Further, the arithmetic part 210 displays the measured Hartmann image and the optical characteristic such as the ocular higher order aberrations on the display part 230 (S121).

Besides, instead of the steps S117 to S121 or in parallel to them, the arithmetic part 210 may capture the second light receiving signal concerning the anterior eye image by the second light receiving part 35 and may calculate the optical characteristic such as higher order aberrations (corneal higher order aberrations) occurring at the cornea, and the corneal shape. After capturing the second light receiving signal, the arithmetic part 210 analyzes the position of a ring image appearing substantially concentrically with respect to the bright point of reflection of the corneal vertex by using an image processing technique. With respect to the position of the ring, for example, about 256 points are acquired over 360 degrees on the circumference. Besides, the arithmetic part 210 calculates the tilt of the cornea from the position of the ring. Besides, the arithmetic part 210 calculates the height of the cornea from the tilt of the cornea, and treats the cornea similarly to an optical lens to calculate the optical characteristic. The higher order aberrations (corneal higher order aberrations) occurring at the cornea are obtained by the second light receiving signal. The arithmetic part 210 displays the calculated corneal higher order aberrations, the corneal shape and the like on the display part 230. Further, the arithmetic part 210 calculates the white light MTF, Strehl ratio, Landolt's ring pattern and the like and may display them on the display part 230.

The arithmetic part 210 returns to the step S101 to continue to measure, otherwise it terminates the processing (S123).

Figure 11:
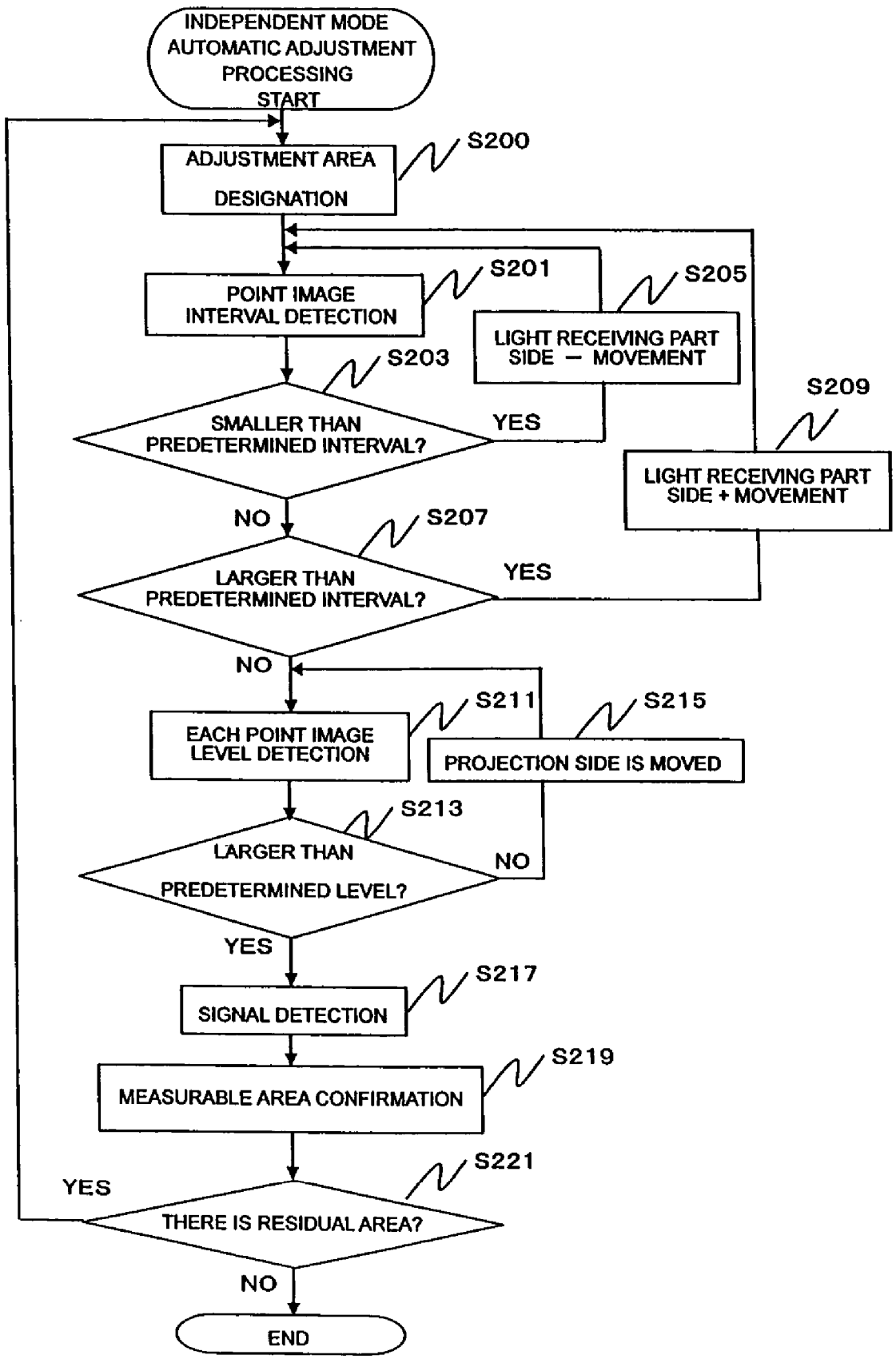
FIG. 11 is a flowchart of an independent mode automatic adjustment processing.

FIG. 11 shows a flowchart of the independent mode automatic adjustment processing. First, the arithmetic part 210 refers to the measurable identification information of the measurement data of the memory 240, and specifies an adjustment area from the unmeasurable areas in which an adjustment is to be made by moving the first illumination optical system 10 and the first light receiving optical system 20 so that the area becomes a measurable area (S200).

Next, the arithmetic part 210 reads out the first light receiving signal from the first light receiving part 23, detects intervals of the respective point images in the adjustment area on the basis of the read first light receiving signal, and obtains an average of the point image intervals (S201). The arithmetic part 210 reads out a previously set predetermined interval from the memory 240, and compares it with the average point image interval of the adjustment area. In the case where the average point image interval of the adjustment area is smaller than the previously set predetermined interval (S203), the arithmetic part 210 outputs a signal to the second driving part 260 to move the first light receiving optical system 20 (light receiving side) in the− direction, and returns to the processing of the step S201 (S205).

In the case where the average point image interval of the adjustment area is larger than the predetermined interval (S207), the arithmetic part 210 outputs a signal to the second driving part 260 to move the first light receiving optical system 20 in the+ direction, and returns to the processing of the step S201 (S209). The second driving part 260 receives the signal from the arithmetic part 210, and drives the second movement means 120 in accordance with the received signal. Besides, in the case where the average point image interval of the adjustment area is the predetermined interval, the arithmetic part 210 proceeds to the processing of step S211. Incidentally, with respect to the comparison of the point image interval with the predetermined interval, in addition to the average of the respective point image intervals detected at the step S201, a suitable value such as a minimum value, a maximum value, or a summation may be used. Besides, in addition to the adjustment of the light receiving side on the basis of the point image interval, an adjustment may be made on the basis of point image density. In this case, the arithmetic part 210 obtains the point image density of the adjustment area on the basis of the first light receiving signal, and further reads out the previously set predetermined density range from the memory 240. In the case where the point image density is larger than the predetermined range, the arithmetic part 210 outputs a signal to move the light receiving side in the − direction, and in the case where the point image density is smaller than the predetermined range, the arithmetic part outputs a signal to move the light receiving side in the+ direction.

Next, the arithmetic part 210 reads out the first light receiving signal from the first light receiving part 23, detects the point image levels on the basis of the read first light receiving signal, and obtains the average of the point image levels of the adjustment area (S211). The arithmetic part 210 reads out the previously set predetermined level from the memory 240, and judges whether the average point image level of the adjustment area is larger than the predetermined level (S213). Incidentally, with respect to the comparison of the point image level with the predetermined level, in addition to the average of the respective point image levels detected at the step S211, a suitable value such as a minimum value, a maximum value or a summation may be used. In the case where the average point image level of the adjustment area is smaller than the predetermined level (S213), the arithmetic part 210 outputs a signal to the first driving part 250 to move the first illumination optical system 10 (projection side), and returns to the processing of the step S211 (S215). With respect to the movement direction of the first illumination optical system 10, a judgment is made as to whether the point image level becomes large when it is moved in an arbitrary direction, and it may be moved in the direction where the point image level becomes large. Besides, the arithmetic part 210 may move the first illumination optical system 10 so that the point image level becomes maximum. The first driving part 250 receives the signal from the arithmetic part 210, and moves the first illumination optical system 10 by the first movement means 110 in accordance with the received signal. On the other hand, in the case where the average point image level of the adjustment area is larger than the predetermined level (S213), the arithmetic part 210 proceeds to step S217.

The arithmetic part 210 receives the first light receiving signal from the first light receiving part 23, and stores diopter values (measurement condition) consistent with the positions of the projection side and the light receiving side and the coordinates (measurement value) of the point image based on the received first light receiving signal, which are made to correspond to the data identifier, into the measurement data of the memory 240 (S217). Incidentally, the arithmetic part 210 may store the measurement value which is made to correspond to the area identifier for each area.

The arithmetic part 210 obtains the density distribution of point images of the inputted first light receiving signal, and judges whether the adjustment area is measurable (S219). The judgment on the measurability can be made the same as the step 109. Further, the arithmetic part 210 judges whether another area is also a measurable area. Incidentally, the arithmetic part 210 refers to the measurable identification information of the measurement data stored in the memory 240, and may judge whether it is measurable only with respect to an unmeasurable area. The arithmetic part 210 stores the measurable identification information indicating measurability or unmeasurability, which is made to correspond to the data identifier and the area identifier of each area, into the measurement data of the memory 240.

The arithmetic part 210 further refers to the measurable identification information of the memory 240, and judges whether there is an area in which a measurable point image coordinate has not been obtained (S221). When judging that the unmeasurable area exists, the arithmetic part 210 returns to the step S200, and on the other hand, in the case where the unmeasurable area does not exist, the arithmetic part ends the independent mode automatic adjustment processing, and proceeds to the processing of the step S115.

Figure 12:
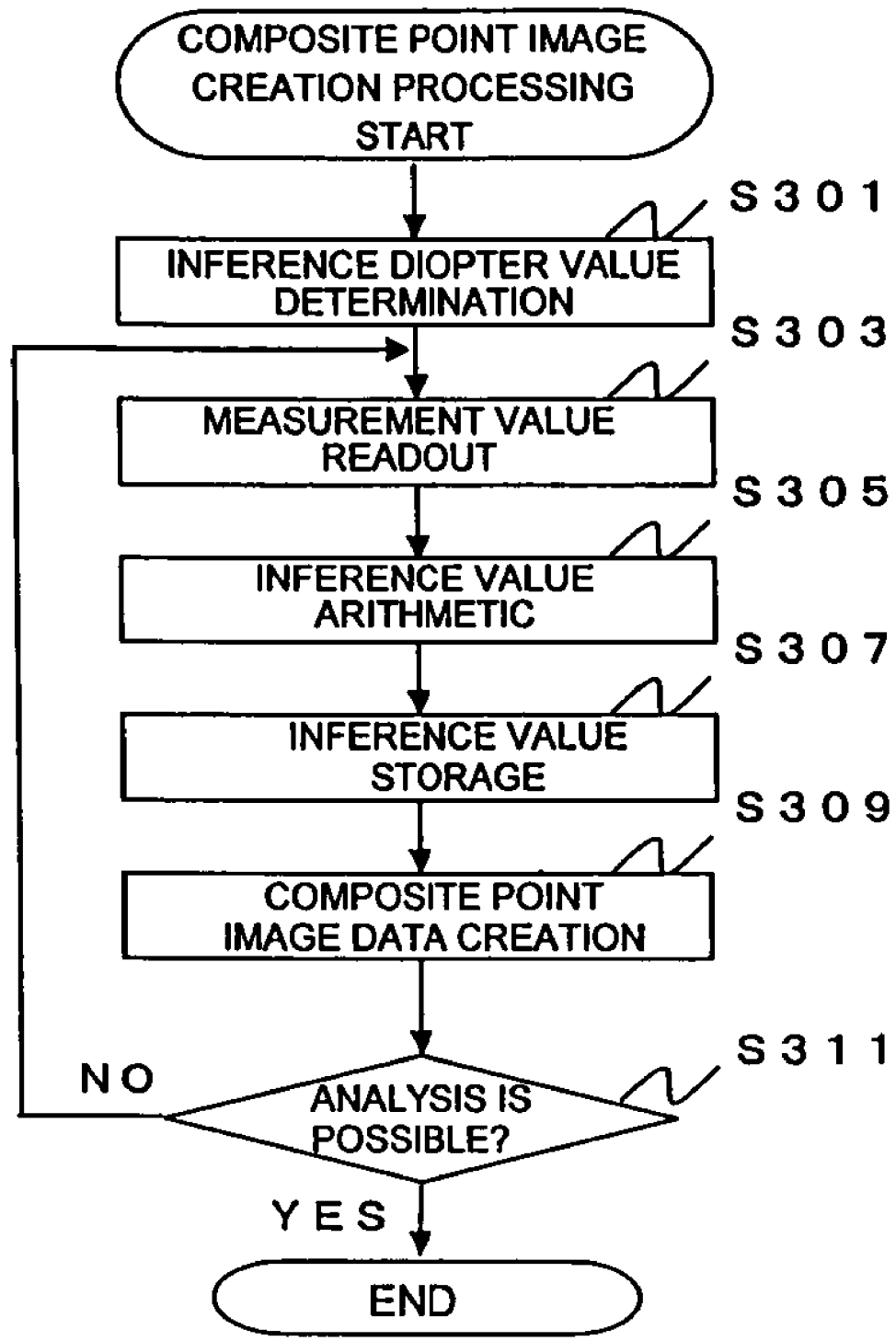
FIG. 12 is a flowchart of a composite point image creation processing.

FIG. 12 shows a flowchart of a composite point image creation processing. Although a method of creating a composite point image from two measurement data will be described below, a composite point image can be created similarly with respect to three or more data. First, the arithmetic part 210 sequentially reads out measured diopter values from the measurement conditions of the measurement data stored in the memory 240, and obtains an average of the diopter values (in the case of two measurement data, it becomes a center diopter value) (S301). For example, the arithmetic part 210 infers point image coordinates in a case where a measurement is made while the average of the diopter values is made the measurement condition, and combines the inferred point image coordinates to create the composite point image. Besides, with respect to the calculation of the average of the diopter values, both the projection side and the light receiving side may be used, or either one may be used. Incidentally, in addition to the average diopter value, a suitable diopter value is used and point image coordinates can also be inferred.

The arithmetic part 210 reads out the measurement conditions and the measurement values from the measurement data stored in the memory 240 (S303). Further, the arithmetic part 210 receives a pupil radius and a distance between the Hartmann plate 22 and the first light receiving part 23 from the memory 240 or the input part 270, and obtains an average diopter value, that is, an inference value of point image coordinates under a measurement condition other than the measured diopter value (S305). Hereinafter, the inference of the point image coordinates will be described.

For example, after the Hartmann images of plural screens are acquired, from the barycentric position of the point images which can be detected from those, it is possible to infer the barycentric position of point images under a measurement condition other than the measured diopter values (for example, position of the center value of the acquired diopter values). A movement amount of the point image is obtained from the image of the first light receiving part 23, and the movement amount of an i-th point image is made $\Delta x_i$, $\Delta y_i$. The movement amount and the higher order aberrations are correlated with each other by the following partial differentiation equation.

$$\frac{\partial W(X,Y)}{\partial X} = \frac{\Delta x_i}{f} \qquad \text{[Numerical Expression 5]}$$

$$\frac{\partial W(X,Y)}{\partial Y} = \frac{\Delta y_i}{f}$$

(f: distance between the Hartmann plate 22 and the first light receiving part 23)

Here, when the wavefront W is expressed by expansion using Zernike polynomials $Z_i^{2j-1}$, the following expression is obtained.

$$W(X,Y) = \sum_{i=0}^{n} \sum_{j=0}^{i} c_i^{2j-i} Z_i^{2j-i}(X,Y) \qquad \text{[Numerical Expression 6]}$$

Besides, by the change of the diopter position, with respect to the wavefront W, only the Zernike coefficient $C_2^0$ corresponding to the diopter is changed. It is conceivable that the barycentric position of the point images is moved only by this change.

When a barycentric position of point images at the measured diopter positions is $(X_{i1}, Y_{i1})$, a barycentric position of point images at inference (analysis) diopter positions is $(X_i, Y_i)$, a movement amount is $\Delta X_{i1}$, $\Delta Y_{i1}$, a Zernike coefficient change amount is $(C_2^0)'$, and a distance between the Hartmann plate 22 and the first light receiving part 23 is F, the relation of the following expression is established.

$$X_i = \Delta X_{i1} + X_{i1} \qquad \text{[Numerical Expression 7]}$$
$$= \frac{\partial}{\partial X}\{\Delta(c_2^0)' Z_2^0(X_{i1}, Y_{i1})\} \cdot F + X_{i1}$$
$$= \Delta(c_2^0)' \frac{\partial}{\partial X} Z_2^0(X_{i1}, Y_{i1}) \cdot F + X_{i1}$$

$$Y_i = \Delta Y_{i1} + Y_{i1}$$
$$= \frac{\partial}{\partial Y}\{\Delta(c_2^0)' Z_2^0(X_{i1}, Y_{i1})\} \cdot F + Y_{i1}$$
$$= \Delta(c_2^0)' \frac{\partial}{\partial Y} Z_2^0(X_{i1}, Y_{i1}) \cdot F + Y_{i1}$$

Besides, an expression for calculating the Zernike coefficient $\Delta(C_2^0)'$ from the diopter change amount $\Delta S_1$ is expressed by the following expression.

$$\Delta(c_2^0)' = -\frac{1}{4} \Delta S_1 \cdot r^2 \qquad \text{[Numerical Expression 8]}$$

Where, r is a pupil radius (mm). Besides, the Zernike polynomial $Z_2^0$ is expressed by the following expression from FIG. 18.

$$Z_2^0 = 2X^2 + 2Y^2 - 1 \qquad \text{[Numerical Expression 9]}$$

Thus, the barycentric position $(X_{ia}, Y_{ia})$ of the point images at the inference diopter position can be expressed by the following expression when the barycentric position of the point images at the measured diopter value "a" used for the inference is made $(X_{i1a}, Y_{i1a})$.

$$X_{ia} = -\frac{1}{4} \Delta S_1 \cdot r^2 \cdot 4 X_{i1a} \cdot F + X_{i1a} \qquad \text{[Numerical Expression 10]}$$
$$= -\Delta S_1 \cdot r^2 \cdot X_{i1a} \cdot F + X_{i1a}$$

$$Y_{ia} = -\frac{1}{4} \Delta S_1 \cdot r^2 \cdot 4 Y_{i1a} \cdot F + Y_{i1a}$$
$$= -\Delta S_1 \cdot r^2 \cdot Y_{i1a} \cdot F + Y_{i1a}$$

In the same way, it is also possible to infer the barycentric position of point images from other measurement data. For example, a barycentric position $(X_{ib}, Y_{ib})$ of point images at an inference (analysis) diopter position is expressed by the following expression when a barycentric position of point images at a measured diopter position "b" used for inference is $(X_{i2b}, Y_{i2b})$, and a diopter change amount is $\Delta S_2$.

$$X_{ib} = -\frac{1}{4} \Delta S_2 \cdot r^2 \cdot 4 X_{i2b} \cdot F + X_{i2b} \qquad \text{[Numerical Expression 11]}$$
$$= -\Delta S_2 \cdot r^2 \cdot X_{i2b} \cdot F + X_{i2b}$$

$$Y_{ib} = -\frac{1}{4} \Delta S_2 \cdot r^2 \cdot 4 Y_{i2b} \cdot F + Y_{i2b}$$
$$= -\Delta S_2 \cdot r^2 \cdot Y_{i2b} \cdot F + Y_{i2b}$$

When the wavefront W is calculated on the basis of the barycentric positions obtained by combining these, a result incorporating the barycentric positions obtained by the plural screens can be obtained. For example, in the Hartmann images i=1 to 100 of two screens, in the case where measurable point images at position "a" are i=1 to 50, and measurable point images at position "b" are i=51 to 100, the barycentric position of composite point images is obtained by $$X_i = (X_{1a}, X_{2a}, \ldots, X_{50a}, X_{51b}, X_{52b}, \ldots X_{99b}, X_{100b})$$

$$Y_i = (Y_{1a}, Y_{2a}, \ldots, Y_{50a}, Y_{51b}, Y_{52b}, \ldots, Y_{99b}, Y_{100b})$$
[Numerical Expression 12]

The arithmetic part 210 uses the numerical expression 10 to calculate the inference value (S305), and stores the obtained inference value, which is made to correspond to the data identifier and the area identifier, into the inference data of the memory 240 (S307).

Besides, the arithmetic part 210 refers to the measurable identification information corresponding to the data identifier of the measurement data stored in the memory 240, and judges the measurable area. Incidentally, the arithmetic part 210 may store the measurable identification information which is made to correspond to the data identifier of the inference data and each area identifier. Further, the arithmetic part 210 extracts inference values of point images belonging to the measurable area from the inference data, and stores the extracted inference values into the composite point image data of the memory 240 (S309). Incidentally, with respect to the area in which an inference value is already stored, they may not be stored or may overwrite it to store.

Next, the arithmetic part 210 judges whether the composite point image data is analyzable data (S311). For example, the arithmetic part 210 can judge by whether data of all areas are stored in the composite point image data, or whether the number of the composite point image data is a predetermined number of point images or larger. Incidentally, as a judgment standard, a suitable one may be used. In the case where the composite point image data is analyzable, the arithmetic part 210 ends the composite point image creation processing, and proceeds to step S117, and on the other hand, in the case where it is not analyzable, the arithmetic part returns to the step S303, and obtains an inference value from another measurement value.

Incidentally, as the storage format of data and the creation procedure of the composite point image, a suitable method other than the above can be adopted. For example, all inference data may be first obtained from the measurement data, or measurement data may be selected so that measurement data used for the creation of composite point images becomes as small as possible.

Figure 13:
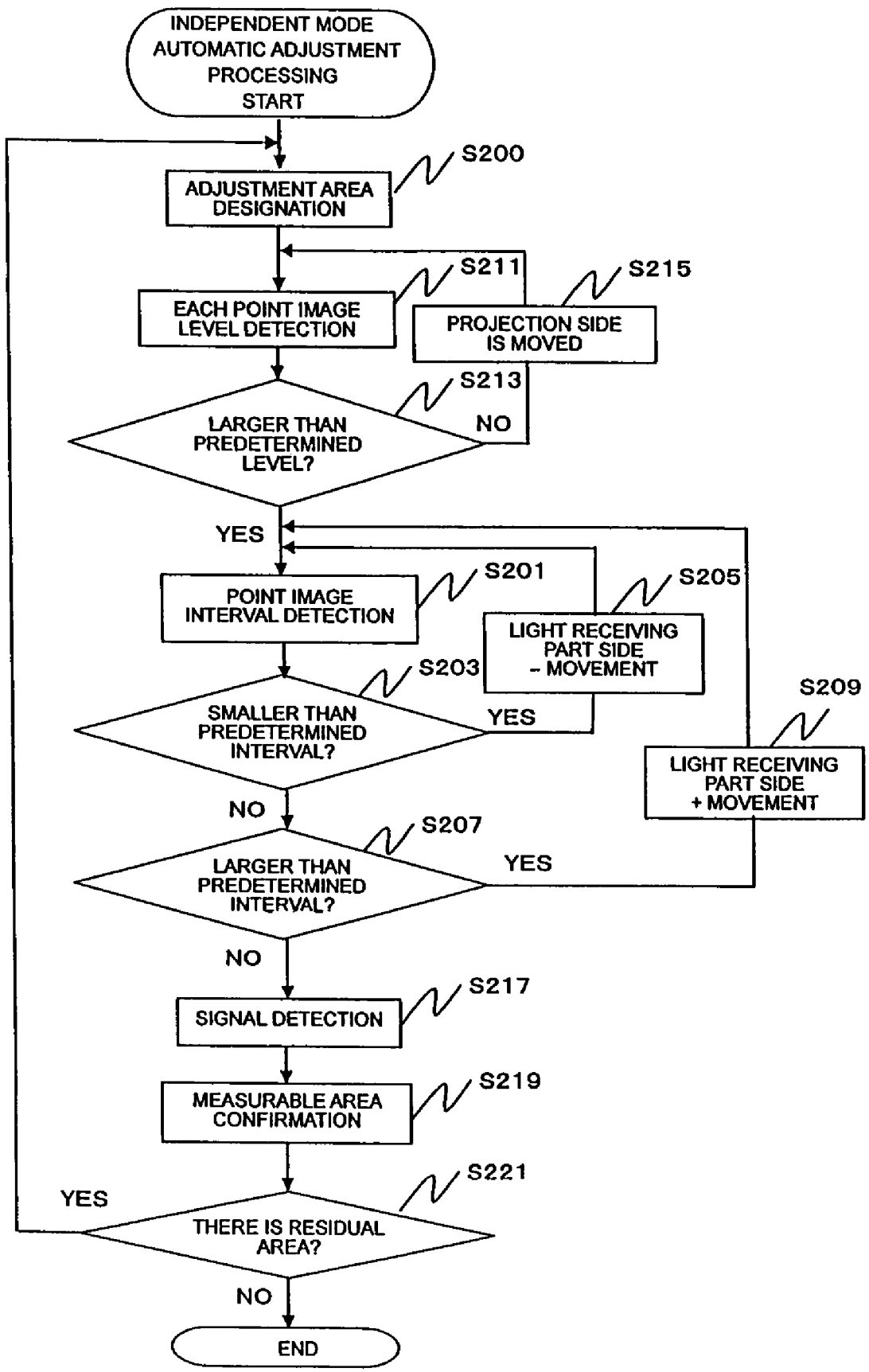
FIG. 13 is a view showing a first modified example of the independent mode automatic adjustment processing.

FIG. 13 shows a first modified example of the independent mode automatic adjustment processing. In the modified example of FIG. 13, the order of the movement (S211 to S215) of the projection side on the basis of the point image level in FIG. 11 and the movement (S201 to S209) of the light receiving side on the basis of the point image interval is reversed in the flowchart. Since processings of the respective steps are the same as FIG. 11, the same symbols as FIG. 11 are given and the explanation will be omitted.

Figure 14:
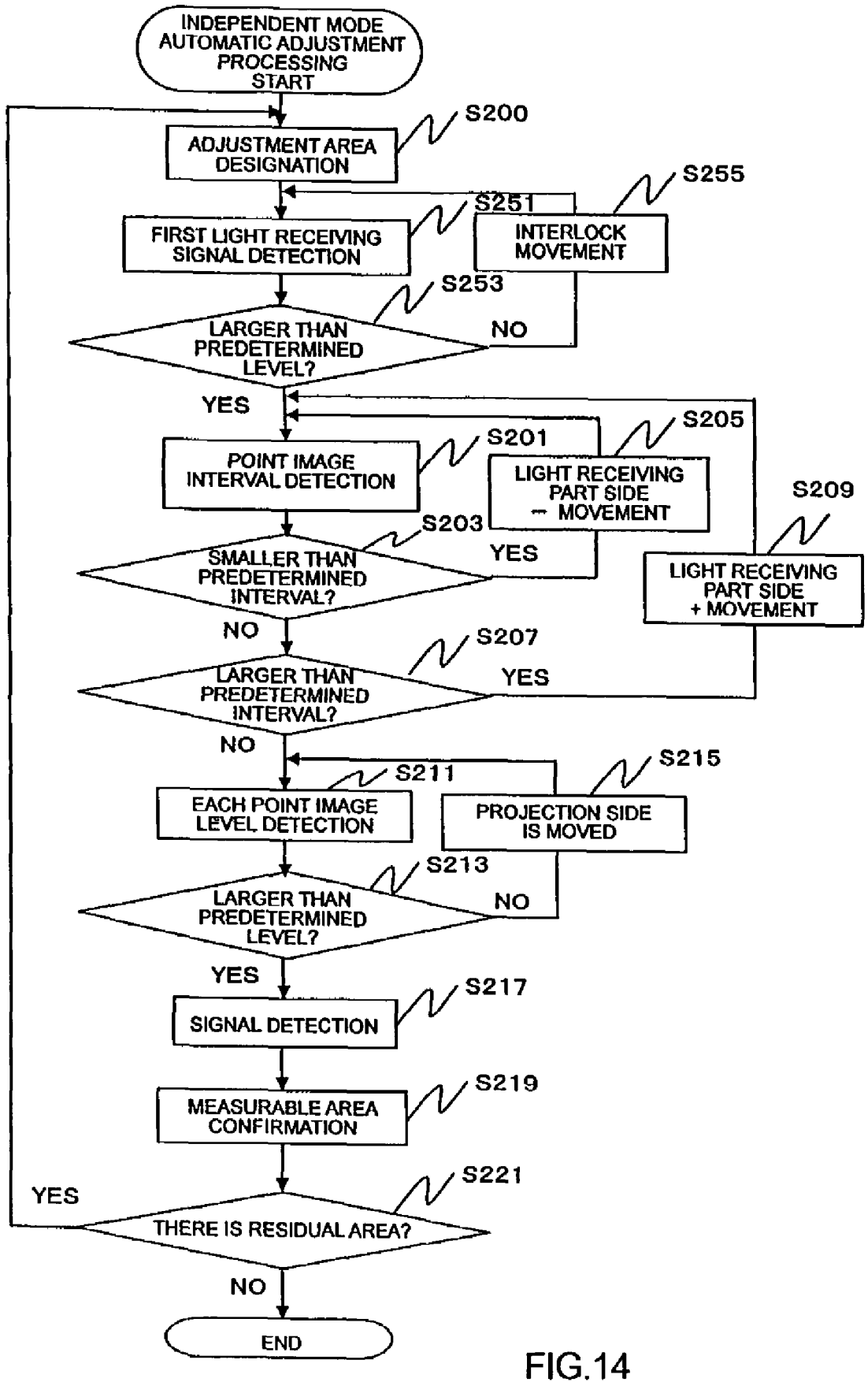
FIG. 14 is a view showing a second modified example of the independent mode automatic adjustment processing.

FIG. 14 shows a second modified example of the independent mode automatic adjustment processing. In the modified example shown in FIG. 14, before an adjustment is made in the independent mode, the projection side and the light receiving side are interlocked and adjusted in the interlock mode. Especially, it is effective in the case where the eye characteristics of a measurable area and an unmeasurable area are largely different from each other.

First, the arithmetic part carries out a processing of step S200. Since the details of the processing are the same as the above, the explanation will be omitted. Next, the arithmetic part 210 captures a first light receiving signal concerning a Hartmann image by using the first light receiving part 23 of low noise CCDs or the like (S251). The arithmetic part 210 obtains an average of light receiving signal levels concerning the inputted first light receiving signal.

The arithmetic part 210 reads a predetermined signal level from the memory 240, and judges whether the average of the light receiving signal levels is larger than the predetermined signal level (S253). Incidentally, the predetermined signal level is previously set and is stored in the memory 240. Incidentally, in addition to the use of the average of the light receiving signal levels, a suitable value such as a minimum value, a maximum value or a summation may be used.

In the case where the average light receiving signal level is lower than the predetermined signal level (S253), the arithmetic part 210 outputs movement signals to the first driving part 250 and the second driving part 260 automatically or by the instructions from the input part 270 to interlock and move the first illumination optical system 10 and the first light receiving optical system 20, and returns to the step S251 (S255). The first driving part 250 and the second driving part 260 receive the movement signals from the arithmetic part 210, and interlock and move the first illumination optical system 10 and the first light receiving optical system 20 by the first movement means 110 and the second movement means 120 in accordance with the received signals. Besides, the arithmetic part 210 may move the first illumination optical system 10 and the first light receiving optical system 20 so that the signal level from the first light receiving part 23 becomes maximum.

On the other hand, in the case where the average light receiving signal level is larger than the predetermined signal level (S253), the arithmetic part 210 carries out the processings of step S201 to step S221. Since the details of the respective processings are the same as FIG. 11, the same symbols as FIG. 11 are given and the explanation will be omitted.

Figure 15:
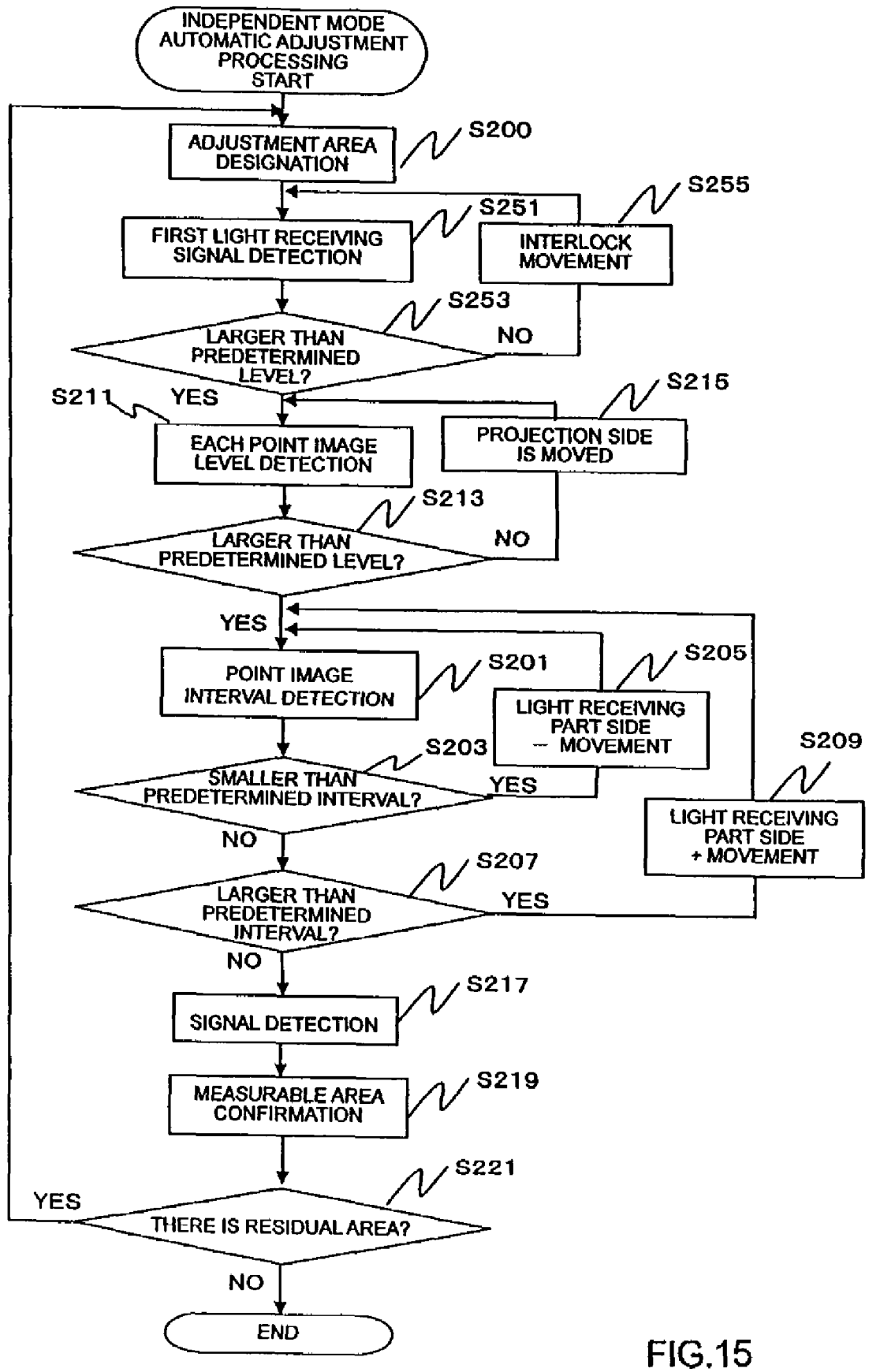
FIG. 15 is a view showing a third modified example of the independent mode automatic adjustment processing.

FIG. 15 shows a third modified example of the independent mode automatic adjustment processing. In the modified example shown in FIG. 15, the order of the adjustment (S211 to S215) of the projection side on the basis of the point image level in FIG. 14 and the adjustment (S201 to S209) of the light receiving side on the basis of the point image interval is reversed. Since the processings of the respective steps are the same as FIG. 14, the same symbols as FIG. 14 are given and the explanation will be omitted.

Figure 16:
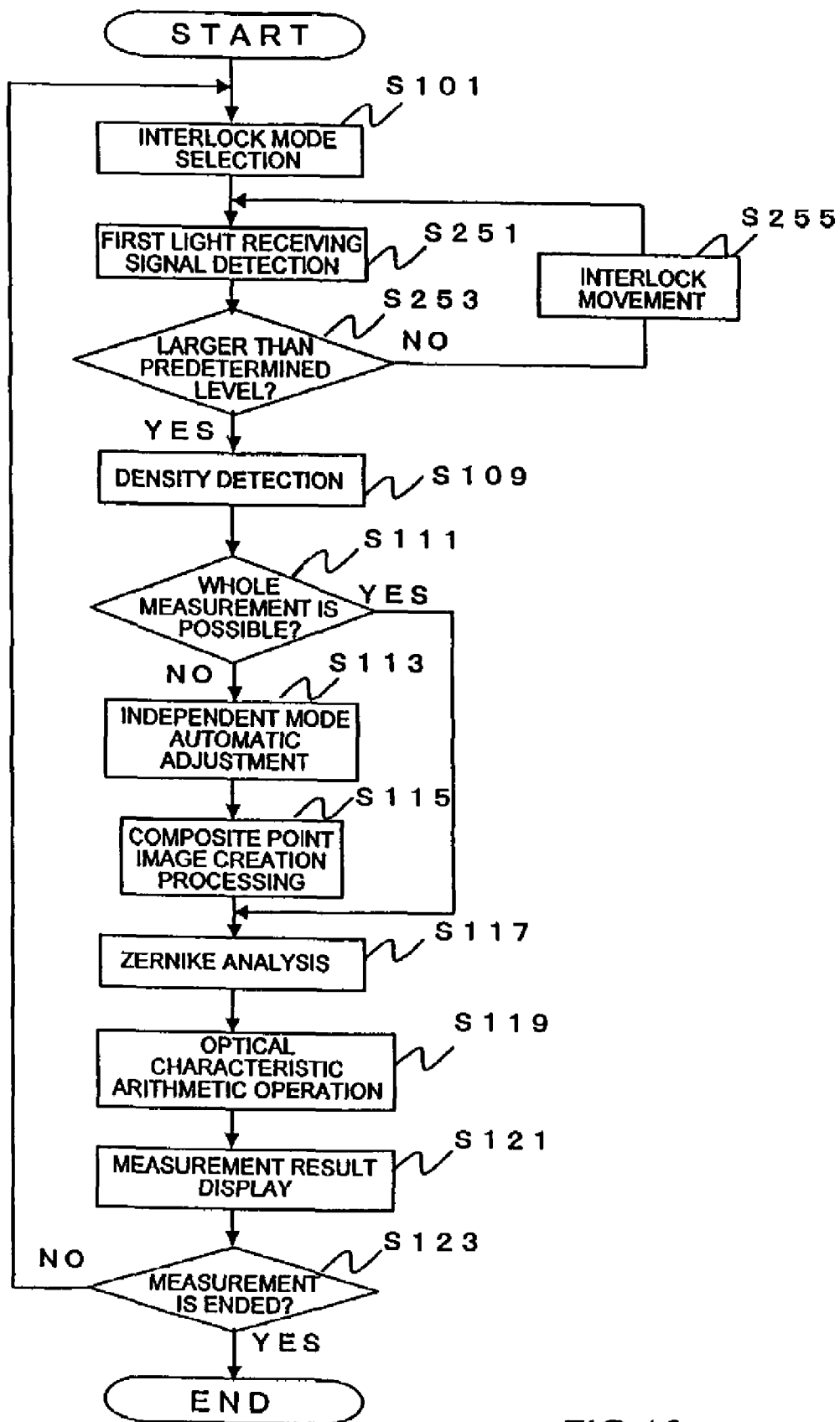
FIG. 16 is a view showing a modified example of a flowchart for obtaining the optical characteristic of the subject eye by combining Hartmann images.

FIG. 16 shows a modified example of a flowchart for obtaining the optical characteristic of the subject eye 60 by combining plural Hartmann images. In the modified example shown in FIG. 16, the arithmetic part 210 adjusts the first illumination optical system 10 and the first light receiving optical system 20 on the basis of the signal level of the first light receiving signal from the first light receiving part 23, and detects the density of the point images from the Hartmann images at that time.

Since the processings of the respective steps are the same as the steps with the same symbols of FIG. 10 and FIG. 14, the explanation will be omitted. However, at step S253, in the case where the average light receiving signal level is larger than the predetermined signal level, the arithmetic part 210 proceeds to the processing of step S109.

According to the present invention, there is provided an ophthalmic measuring apparatus capable of measuring even an eye which can not be measured through a conventional uniform adjustment because of a large difference in the distribution of a refractive index, refraction or aberration, or the like. Besides, according to the invention, there is provided an apparatus in which an automatic adjustment is made to obtain necessary point image data so that Hartmann images are automatically obtained, and an optical characteristic is obtained by combining the acquired Hartmann images.

This application claims priority from Japanese Patent Application 2002-302435, filed Oct. 17, 2002, which is incorporated herein by reference in its entirety.

What is claimed is:

1. An ophthalmic measuring apparatus, comprising:
a first illumination optical system including a first light source to emit a light flux of a first wavelength, and for illuminating to be condensed on a vicinity of a retina of a subject eye with a first illumination light flux from the first light source;
a first light receiving optical system including a first conversion member to convert a reflected light flux reflected from the retina of the subject eye into at least 17 beams and a first light receiving part to receive the plural light fluxes converted by the first conversion member as first and second signals, and the first light receiving optical system is for guiding the reflected light flux to the first light receiving part by lenses;
first movement means for moving a light condensing position of the first illumination optical system;
second movement means for optically moving the first light receiving part and the first conversion member;
an adjustment part configured to adjust positions of the first illumination optical system and the first light receiving optical system by the first and the second movement means to measure the first and second signals under plural measurement conditions until a measurement of an optical characteristic of the subject eye is enabled by combining at least the first and second signals from the first light receiving part; and
an arithmetic part configured to obtain the optical characteristic of the subject eye by combining the first and second signals obtained from the first light receiving part under the plural measurement conditions in a process of adjustment of the adjustment part,
wherein,
the arithmetic part is configured to obtain a density of point images or an interval of point images or a point image level from the first signals of the first light receiving part, and judge whether there is a region in which the density of point images or the interval of point images or the point image level is outside the predetermined range,
in case where there is such a region, the adjustment part controls the first and the second movement means so that the density of point images or the interval of point images or the point image level of the region falls within the predetermined range and,
the arithmetic part is configured to input the second signals from the first light receiving part, combine the first and second signals, and obtain the optical characteristic of the subject eye based on the combined signals.

2. An ophthalmic measuring apparatus according to claim 1, wherein the arithmetic part combines tilt angle data of the reflected light flux obtained by the first light receiving part under the plural measurement conditions and performs a Zernike analysis on the basis of the combined tilt angle data to obtain the optical characteristic of the subject eye.

3. An ophthalmic measuring apparatus according to claim 1, wherein the arithmetic part sets other measurement conditions different from the plural measurement conditions in accordance with the plural measurement conditions under which the measurement is made in the process of the adjustment of the adjustment part, infers point image data in a case where a measurement is made under the other set measurement conditions on the basis of the first and second signals obtained by the first light receiving part, and combines the inferred data.

4. An ophthalmic measuring apparatus according to claim 1, wherein the arithmetic part obtains a density of point images or an interval thereof from the first signals of the first light receiving part, and judges that an area in which the point image density or interval is within a predetermined range is a measurable area, and an area in which the point image density or interval is outside the predetermined range is an unmeasurable area, and
the adjustment part controls the first and the second movement means so that the point image density or interval of the unmeasurable area falls within the predetermined range.

5. An ophthalmic measuring apparatus according to claim 4, wherein the adjustment part adjusts the position of the first light receiving optical system by the second movement means to a minus side in a case where there is a region in which the point image density on the basis of the first signals of the first light receiving part is larger than the predetermined range or the point image interval is narrower than the predetermined range, and to a plus side in a case where there is a region in which the point image density is smaller than the predetermined range or the point image interval is wider than the predetermined range.

6. An ophthalmic measuring apparatus according to claim 1, wherein the arithmetic part obtains a maximal value of respective point image levels on the basis of the first signals obtained from the first light receiving part, and judges that an area in which the maximal value is within a predetermined range is a measurable area, and an area in which the maximal value is outside the predetermined range is an unmeasurable area, and
the adjustment part controls the first and the second movement means so that the maximal value of the respective point image levels of the unmeasurable area falls within the predetermined range.

7. An ophthalmic measuring apparatus according to claim 1, further comprising:
a refraction measuring illumination optical system for irradiating a pattern for refraction measurement to the retina of the subject eye; and
a refraction measuring light receiving optical system for receiving a pattern image projected on the retina of the subject eye by the refraction measuring illumination optical system, wherein
the arithmetic part obtains refraction from the pattern image received by the refraction measuring light receiving optical system, and
the adjustment part moves the first illumination optical system and the first light receiving optical system by the first and the second movement means on the basis of the refraction.

8. An ophthalmic measuring apparatus according to claim 1, further comprising:

a mode changeover part for switching between an interlock mode for interlocking movement operations of the first movement means and the second movement means, and an independent mode in which the first movement means and the second movement means can be independently controlled, wherein the arithmetic part combines the first and second signals obtained by the first light receiving part under the plural measurement conditions in a process of adjustment in the respective modes, and obtains the optical characteristic of the subject eye.

9. An ophthalmic measuring apparatus according to claim 1, wherein, the plural measurement conditions are plural diopter positions of the first illumination optical system and the first light receiving optical system adjusted by the adjustment part, the arithmetic part combines, according to each diopter value corresponding to the diopter positions, barycentric positions of point images of the first and second signals obtained under the plural measurement conditions.

* * * * *